United States Patent [19]
von der Osten et al.

[11] Patent Number: 6,017,751
[45] Date of Patent: Jan. 25, 2000

[54] PROCESS AND COMPOSITION FOR DESIZING CELLULOSIC FABRIC WITH AN ENZYME HYBRID

[75] Inventors: Claus von der Osten, Lyngby; Mads E. Bjornvad, Frederiksberg; Jesper Vind, Lyngby; Michael Dolberg Rasmussen, Vallensbaek, all of Denmark

[73] Assignee: Novo Nordisk A/S, Bagsværd, Denmark

[21] Appl. No.: 08/812,829

[22] Filed: Mar. 6, 1997

Related U.S. Application Data

[63] Continuation of application No. PCT/DK97/00041, Jan. 29, 1997.

[30] Foreign Application Priority Data

Jan. 29, 1996 [DK] Denmark .................................. 0093/96

[51] Int. Cl.⁷ .......................... D06M 16/00; C12P 21/04; C11D 7/42; C12N 9/28
[52] U.S. Cl. ........................ 435/263; 435/69.7; 435/71.1; 435/198; 435/202; 510/530
[58] Field of Search ................. 435/69.7, 71.1, 435/202, 198, 263; 510/530

[56] References Cited

U.S. PATENT DOCUMENTS

| | | | |
|---|---|---|---|
| 5,525,193 | 6/1996 | Franks et al. ............................... | 162/5 |
| 5,536,655 | 7/1996 | Thomas et al. .......................... | 435/209 |
| 5,578,489 | 11/1996 | Petersen ................... | 435/263 |

FOREIGN PATENT DOCUMENTS

| | | |
|---|---|---|
| WO 90/00609 | 1/1990 | WIPO . |
| WO 91/10732 | 7/1991 | WIPO . |
| WO 91/17244 | 11/1991 | WIPO . |
| WO 93/05226 | 3/1993 | WIPO . |
| WO 93/11249 | 6/1993 | WIPO . |
| WO 94/07998 | 4/1994 | WIPO . |
| WO 94/24158 | 10/1994 | WIPO . |
| WO 95/16782 | 6/1995 | WIPO . |
| WO 96/13524 | 5/1996 | WIPO . |
| WP 96/34092 | 10/1996 | WIPO . |
| WO 97/28243 | 8/1997 | WIPO . |

OTHER PUBLICATIONS

Greenwood et al. Biotech. & Bioeng. Accession No. 11434006, 1994, 44(II) 1295–1305.

Chalfie et al. (1994) Science 263:802–805.

*Primary Examiner*—David M. Naff
*Attorney, Agent, or Firm*—Steve T. Zelson, Esq.; Reza Green, Esq.

[57] ABSTRACT

Cellulose-containing fabric is desized by treating with an enzyme hybrid having a catalytically active amino acid sequence of an enzyme such as a lipase or an amylase linked to an amino acid sequence containing a cellulose-binding domain. The enzyme amino acid sequence may be of an α-amylase obtainable from a species of Bacillus such as *Bacillus licheniformis*, or of a lipase obtainable from a species of Humicola, Candida, Pseudomonas or Bacillus. The cellulose-binding domain may be from a cellulase, a xylanase, a mannanase, an arabinofuranosidase, an acetylesterase or a chitinase. The enzyme hybrid is obtained from a transformed host cell containing an expression cassette having a DNA sequence encoding the enzyme hybrid. A desizing composition is formed containing the enzyme hybrid and a wetting agent.

9 Claims, No Drawings

SEQUENCE LISTING (1) GENERAL INFORMATION:

(iii) NUMBER OF SEQUENCES: 31

(2) INFORMATION FOR SEQ ID NO: 1:

(i) SEQUENCE CHARACTERISTICS:
    (A) LENGTH: 2253 base pairs
    (B) TYPE: nucleic acid
    (C) STRANDEDNESS: single
    (D) TOPOLOGY: linear (ii) MOLECULE TYPE: DNA (genomic)

(xi) SEQUENCE DESCRIPTION: SEQ ID NO: 1:

```
ATGAAACAAC AAAAACGGCT TTACGCCCGA TTGCTGACGC TGTTATTTGC GCTCATCTTC      60

TTGCTGCCTC ATTCTGCAGC AGCGGCGGCA AATCTTAATG GGACGCTGAT GCAGTATTTT     120

GAATGGTACA TGCCCAATGA CGGCCAACAT TGGAAGCGTT TGCAAAACGA CTCGGCATAT     180

TTGGCTGAAC ACGGTATTAC TGCCGTCTGG ATTCCCCCGG CATATAAGGG AACGAGCCAA     240

GCGGATGTGG GCTACGGTGC TTACGACCTT TATGATTTAG GGGAGTTTCA TCAAAAAGGG     300

ACGGTTCGGA CAAAGTACGG CACAAAAGGA GAGCTGCAAT CTGCGATCAA AAGTCTTCAT     360

TCCCGCGACA TTAACGTTTA CGGGGATGTG GTCATCAACC ACAAAGGCGG CGCTGATGCG     420

ACCGAAGATG TAACCGCGGT TGAAGTCGAT CCCGCTGACC GCAACCGCGT AATCTCAGGA     480

GAACACCTAA TTAAAGCCTG GACACATTTT CATTTTCCGG GGGCCGGCAG CACATACAGC     540

GATTTTAAAT GGCATTGGTA CCATTTTGAC GGAACCGATT GGGACGAGTC CCGAAAGCTG     600

AACCGCATCT ATAAGTTTCA AGGAAAGGCT TGGGATTGGG AAGTTTCCAA TGAAAACGGC     660

AACTATGATT ATTTGATGTA TGCCGACATC GATTATGACC ATCCTGATGT CGCAGCAGAA     720

ATTAAGAGAT GGGGCACTTG GTATGCCAAT GAACTGCAAT TGGACGGAAA CCGTCTTGAT     780

GCTGTCAAAC ACATTAAATT TTCTTTTTTG CGGGATTGGG TTAATCATGT CAGGGAAAAA     840

ACGGGGAAGG AAATGTTTAC GGTAGCTGAA TATTGGCAGA ATGACTTGGG CGCGCTGGAA     900

AACTATTTGA CAAAACAAA TTTTAATCAT TCAGTGTTTG ACGTGCCGCT TCATTATCAG      960

TTCCATGCTG CATCGACACA GGGAGGCGGC TATGATATGA GGAAATTGCT GAACGGTACG    1020

GTCGTTTCCA AGCATCCGTT GAAATCGGTT ACATTTGTCG ATAACCATGA TACACAGCCG    1080

GGGCAATCGC TTGAGTCGAC TGTCCAAACA TGGTTTAAGC CGCTTGCTTA CGCTTTTATT    1140

CTCACAAGGG AATCTGGATA CCCTCAGGTT TTCTACGGGG ATATGTACGG GACGAAAGGA    1200

GACTCCCAGC GCGAAATTCC TGCCTTGAAA CACAAAATTG AACCGATCTT AAAAGCGAGA    1260

AAACAGTATG CGTACGGAGC ACAGCATGAT TATTTCGACC ACCATGACAT TGTCGGCTGG    1320

ACAAGGGAAG CGACAGCTC GGTTGCAAAT TCAGGTTTGG CGGCATTAAT AACAGACGGA    1380

CCCGGTGGGG CAAAGCGAAT GTATGTCGGC CGGCAAAACG CCGGTGAGAC ATGGCATGAC    1440

ATTACCGGAA ACCGTTCGGA GCCGGTTGTC ATCAATTCGG AAGGCTGGGG AGAGTTTCAC    1500

GTAAACGGCG GATCCGTTTC AATTTATGTT CAAAGATCTG GCGGACCTGG AACGCCAAAT    1560

AATGGCAGAG GAATTGGTTA TATTGAAAAT GGTAATACCG TAACTTACAG CAATATAGAT    1620

TTTGGTAGTG GTGCAACAGG GTTCTCTGCA ACTGTTGCAA CGGAGGTTAA TACCTCAATT    1680

CAAATCCGTT CTGACAGTCC TACCGGAACT CTACTTGGTA CCTTATATGT AAGTTCTACC    1740

GGCAGCTGGA ATACATATCA ACCGTATCTA CAAACATCAG CAAAATTACC GGCGTTCATG    1800

ATATTGTATT GGTATTCTCA GGTCCAGTCA ATGTGGACAA CTTCATATTT AGCAGAAGTT    1860

CACCAGTGCC TGCACCTGGT GATAACACAA GAGACGCATA TTCTATCATT CAGGCCGAGG    1920

ATTATGACAG CAGTTATGGT CCCAACCTTC AAATCTTTAG CTTACCAGGT GGTGGCAGCG    1980

CTTGGCTATA TTGAAAATGG TTATTCCACT ACCTATAAAA ATATTGATTT TGGTGACGGC    2040

GCAACGTCCG TAACAGCAAG AGTAGCTACC CAGAATGCTA CTACCATTCA GGTAAGATTG    2100
```

```
GGAAGTCCAT CGGGTACATT ACTTGGAACA ATTTACGTGG GGTCCACAGG AAGCTTTGAT    2160

ACTTATAGGG ATGTATCCGC TACCATTAGT AATACTGCGG GTGTAAAAGA TATTGTTCTT    2220

GTATTCTCAG GTCCTGTTAA TGTTGACTGG TAG                                 2253
```

(2) INFORMATION FOR SEQ ID NO: 2:

(i) SEQUENCE CHARACTERISTICS:
        (A) LENGTH: 750 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 2:

```
Met Lys Gln Gln Lys Arg Leu Tyr Ala Arg Leu Leu Thr Leu Leu Phe
1               5                   10                  15

Ala Leu Ile Phe Leu Leu Pro His Ser Ala Ala Ala Ala Ala Asn Leu
            20                  25                  30

Asn Gly Thr Leu Met Gln Tyr Phe Glu Trp Tyr Met Pro Asn Asp Gly
        35                  40                  45

Gln His Trp Lys Arg Leu Gln Asn Asp Ser Ala Tyr Leu Ala Glu His
    50                  55                  60

Gly Ile Thr Ala Val Trp Ile Pro Pro Ala Tyr Lys Gly Thr Ser Gln
65                  70                  75                  80

Ala Asp Val Gly Tyr Gly Ala Tyr Asp Leu Tyr Asp Leu Gly Glu Phe
                85                  90                  95

His Gln Lys Gly Thr Val Arg Thr Lys Tyr Gly Thr Lys Gly Glu Leu
            100                 105                 110

Gln Ser Ala Ile Lys Ser Leu His Ser Arg Asp Ile Asn Val Tyr Gly
        115                 120                 125

Asp Val Val Ile Asn His Lys Gly Gly Ala Asp Ala Thr Glu Asp Val
    130                 135                 140

Thr Ala Val Glu Val Asp Pro Ala Asp Arg Asn Arg Val Ile Ser Gly
145                 150                 155                 160

Glu His Leu Ile Lys Ala Trp Thr His Phe His Phe Pro Gly Ala Gly
                165                 170                 175

Ser Thr Tyr Ser Asp Phe Lys Trp His Trp Tyr His Phe Asp Gly Thr
            180                 185                 190

Asp Trp Asp Glu Ser Arg Lys Leu Asn Arg Ile Tyr Lys Phe Gln Gly
        195                 200                 205

Lys Ala Trp Asp Trp Glu Val Ser Asn Glu Asn Gly Asn Tyr Asp Tyr
    210                 215                 220

Leu Met Tyr Ala Asp Ile Asp Tyr Asp His Pro Asp Val Ala Ala Glu
225                 230                 235                 240

Ile Lys Arg Trp Gly Thr Trp Tyr Ala Asn Glu Leu Gln Leu Asp Gly
                245                 250                 255

Asn Arg Leu Asp Ala Val Lys His Ile Lys Phe Ser Phe Leu Arg Asp
            260                 265                 270

Trp Val Asn His Val Arg Glu Lys Thr Gly Lys Glu Met Phe Thr Val
        275                 280                 285

Ala Glu Tyr Trp Gln Asn Asp Leu Gly Ala Leu Glu Asn Tyr Leu Asn
    290                 295                 300

Lys Thr Asn Phe Asn His Ser Val Phe Asp Val Pro Leu His Tyr Gln
305                 310                 315                 320

Phe His Ala Ala Ser Thr Gln Gly Gly Gly Tyr Asp Met Arg Lys Leu
```

```
                    325                 330                 335
Leu Asn Gly Thr Val Val Ser Lys His Pro Leu Lys Ser Val Thr Phe
            340                 345                 350

Val Asp Asn His Asp Thr Gln Pro Gly Gln Ser Leu Glu Ser Thr Val
            355                 360                 365

Gln Thr Trp Phe Lys Pro Leu Ala Tyr Ala Phe Ile Leu Thr Arg Glu
        370                 375                 380

Ser Gly Tyr Pro Gln Val Phe Tyr Gly Asp Met Tyr Gly Thr Lys Gly
385                 390                 395                 400

Asp Ser Gln Arg Glu Ile Pro Ala Leu Lys His Lys Ile Glu Pro Ile
                405                 410                 415

Leu Lys Ala Arg Lys Gln Tyr Ala Tyr Gly Ala Gln His Asp Tyr Phe
            420                 425                 430

Asp His His Asp Ile Val Gly Trp Thr Arg Glu Gly Asp Ser Ser Val
            435                 440                 445

Ala Asn Ser Gly Leu Ala Ala Leu Ile Thr Asp Gly Pro Gly Gly Ala
450                 455                 460

Lys Arg Met Tyr Val Gly Arg Gln Asn Ala Gly Glu Thr Trp His Asp
465                 470                 475                 480

Ile Thr Gly Asn Arg Ser Glu Pro Val Val Ile Asn Ser Glu Gly Trp
                485                 490                 495

Gly Glu Phe His Val Asn Gly Gly Ser Val Ser Ile Tyr Val Gln Arg
                500                 505                 510

Ser Gly Gly Pro Gly Thr Pro Asn Asn Gly Arg Gly Ile Gly Tyr Ile
            515                 520                 525

Glu Asn Gly Asn Thr Val Thr Tyr Ser Asn Ile Asp Phe Gly Ser Gly
530                 535                 540

Ala Thr Gly Phe Ser Ala Thr Val Ala Thr Glu Val Asn Thr Ser Ile
545                 550                 555                 560

Gln Ile Arg Ser Asp Ser Pro Thr Gly Thr Leu Leu Gly Thr Leu Tyr
                565                 570                 575

Val Ser Ser Thr Gly Ser Trp Asn Thr Tyr Gln Pro Tyr Leu Gln Thr
            580                 585                 590

Ser Ala Lys Leu Pro Ala Phe Met Ile Leu Tyr Trp Tyr Ser Gln Val
            595                 600                 605

Gln Ser Met Trp Thr Thr Ser Tyr Leu Ala Glu Val His Gln Cys Leu
        610                 615                 620

His Leu Val Ile Thr Gln Glu Thr His Ile Leu Ser Phe Arg Pro Arg
625                 630                 635                 640

Ile Met Thr Ala Val Met Val Pro Thr Phe Lys Ser Leu Ala Tyr Gln
                645                 650                 655

Val Val Ala Ala Leu Gly Tyr Ile Glu Asn Gly Tyr Ser Thr Thr Tyr
            660                 665                 670

Lys Asn Ile Asp Phe Gly Asp Gly Ala Thr Ser Val Thr Ala Arg Val
            675                 680                 685

Ala Thr Gln Asn Ala Thr Thr Ile Gln Val Arg Leu Gly Ser Pro Ser
        690                 695                 700

Gly Thr Leu Leu Gly Thr Ile Tyr Val Gly Ser Thr Gly Ser Phe Asp
705                 710                 715                 720

Thr Tyr Arg Asp Val Ser Ala Thr Ile Ser Asn Thr Ala Gly Val Lys
                725                 730                 735

Asp Ile Val Leu Val Phe Ser Gly Pro Val Asn Val Asp Trp
            740                 745                 750
```

(2) INFORMATION FOR SEQ ID NO: 3:

(i) SEQUENCE CHARACTERISTICS:
        (A) LENGTH: 1203 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 3:

```
ATGAAAAAGA TAACTACTAT TTTTGTCGTA TTGCTTATGA CAGTGGCGTT GTTCAGTATA     60
GGAAACACGA CTGCTGCTGA TAATGATTCA GTTGTAGAAG AACATGGGCA ATTAAGTATT    120
AGTAACGGTG AATTAGTCAA TGAACGAGGC GAACAAGTTC AGTTAAAAGG GATGAGTTCC    180
CATGGTTTGC AATGGTACGG TCAATTTGTA AACTATGAAA GTATGAAATG CTAAGAGAT    240
GATTGGGGAA TAAATGTATT CCGAGCAGCA ATGTATACCT CTTCAGGAGG ATATATTGAT    300
GATCCATCAG TAAAGGAAAA AGTAAAAGAG GCTGTTGAAG CTGCGATAGA CCTTGATATA    360
TATGTGATCA TTGATTGGCA TATCCTTTCA GACAATGACC AAATATATA TAAAGAAGAA    420
GCGAAGGATT TCTTTGATGA AATGTCAGAG TTGTATGGAG ACTATCCGAA TGTGATATAC    480
GAAATTGCAA ATGAACCGAA TGGTAGTGAT GTTACGTGGG GCAATCAAAT AAAACCGTAT    540
GCAGAGGAAG TCATTCCGAT TATTCGTAAC AATGACCCTA ATAACATTAT TATTGTAGGT    600
ACAGGTACAT GGAGTCAGGA TGTCCATCAT GCAGCTGATA ATCAGCTTGC AGATCCTAAC    660
GTCATGTATG CATTTCATTT TTATGCAGGG ACACATGGTC AAAATTTACG AGACCAAGTA    720
GATTATGCAT TAGATCAAGG AGCAGCGATA TTTGTTAGTG AATGGGGAAC AAGTGCAGCT    780
ACAGGTGATG GTGGCGTGTT TTTAGATGAA GCACAAGTGT GGATTGACTT TATGGATGAA    840
AGAAATTTAA GCTGGGCCAA CTGGTCTCTA ACGCATAAAG ATGAGTCATC TGCAGCGTTA    900
ATGCCAGGTG CAAATCCAAC TGGTGGTTGG ACAGAGGCTG AACTATCTCC ATCTGGTACA    960
TTTGTGAGGG AAAAAATAAG AGAATCAGCA TCTATTCCGC CAAGCGATCC AACACCGCCA   1020
TCTGATCCAG GAGAACCGGA TCCAACGCCC CCAAGTGATC CAGGAGAGTA TCCAGCATGG   1080
GATCCAAATC AAATTTACAC AAATGAAATT GTGTACCATA ACGGCCAGCT ATGGCAAGCA   1140
AAATGGTGGA CACAAAATCA AGAGCCAGGT GACCCGTACG GTCCGTGGGA ACCACTCAAT   1200
TAA                                                                 1203
```

(2) INFORMATION FOR SEQ ID NO: 4:

(i) SEQUENCE CHARACTERISTICS:
        (A) LENGTH: 400 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 4:

```
Met Lys Lys Ile Thr Thr Ile Phe Val Val Leu Leu Met Thr Val Ala
 1               5                  10                  15

Leu Phe Ser Ile Gly Asn Thr Thr Ala Ala Asp Asn Asp Ser Val Val
             20                  25                  30

Glu Glu His Gly Gln Leu Ser Ile Ser Asn Gly Glu Leu Val Asn Glu
         35                  40                  45

Arg Gly Glu Gln Val Gln Leu Lys Gly Met Ser Ser His Gly Leu Gln
     50                  55                  60
```

| | | | | | | | | | | | | | | | |
|---|---|---|---|---|---|---|---|---|---|---|---|---|---|---|---|
|Trp|Tyr|Gly|Gln|Phe|Val|Asn|Tyr|Glu|Ser|Met|Lys|Trp|Leu|Arg|Asp|
|65| | | | |70| | | |75| | | | |80| |

Asp Trp Gly Ile Asn Val Phe Arg Ala Ala Met Tyr Thr Ser Ser Gly
            85                  90                  95

Gly Tyr Ile Asp Asp Pro Ser Val Lys Glu Lys Val Lys Glu Ala Val
            100                 105                 110

Glu Ala Ala Ile Asp Leu Asp Ile Tyr Val Ile Ile Asp Trp His Ile
            115                 120                 125

Leu Ser Asp Asn Asp Pro Asn Ile Tyr Lys Glu Ala Lys Asp Phe
130                 135                 140

Phe Asp Glu Met Ser Glu Leu Tyr Gly Asp Tyr Pro Asn Val Ile Tyr
145                 150                 155                 160

Glu Ile Ala Asn Glu Pro Asn Gly Ser Asp Val Thr Trp Gly Asn Gln
            165                 170                 175

Ile Lys Pro Tyr Ala Glu Glu Val Ile Pro Ile Ile Arg Asn Asn Asp
            180                 185                 190

Pro Asn Asn Ile Ile Ile Val Gly Thr Gly Thr Trp Ser Gln Asp Val
            195                 200                 205

His His Ala Ala Asp Asn Gln Leu Ala Asp Pro Asn Val Met Tyr Ala
            210                 215                 220

Phe His Phe Tyr Ala Gly Thr His Gly Gln Asn Leu Arg Asp Gln Val
225                 230                 235                 240

Asp Tyr Ala Leu Asp Gln Gly Ala Ala Ile Phe Val Ser Glu Trp Gly
            245                 250                 255

Thr Ser Ala Ala Thr Gly Asp Gly Gly Val Phe Leu Asp Glu Ala Gln
            260                 265                 270

Val Trp Ile Asp Phe Met Asp Glu Arg Asn Leu Ser Trp Ala Asn Trp
            275                 280                 285

Ser Leu Thr His Lys Asp Glu Ser Ser Ala Ala Leu Met Pro Gly Ala
290                 295                 300

Asn Pro Thr Gly Gly Trp Thr Glu Ala Glu Leu Ser Pro Ser Gly Thr
305                 310                 315                 320

Phe Val Arg Glu Lys Ile Arg Glu Ser Ala Ser Ile Pro Pro Ser Asp
            325                 330                 335

Pro Thr Pro Pro Ser Asp Pro Gly Glu Pro Asp Pro Thr Pro Pro Ser
            340                 345                 350

Asp Pro Gly Glu Tyr Pro Ala Trp Asp Pro Asn Gln Ile Tyr Thr Asn
            355                 360                 365

Glu Ile Val Tyr His Asn Gly Gln Leu Trp Gln Ala Lys Trp Trp Thr
370                 375                 380

Gln Asn Gln Glu Pro Gly Asp Pro Tyr Gly Pro Trp Glu Pro Leu Asn
385                 390                 395                 400

(2) INFORMATION FOR SEQ ID NO: 5:

(i) SEQUENCE CHARACTERISTICS:
        (A) LENGTH: 1683 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 5:

ATGAAACAAC AAAAACGGCT TTACGCCCGA TTGCTGACGC TGTTATTTGC GCTCATCTTC    60

TTGCTGCCTC ATTCTGCAGC AGCGGCGGCA AATCTTAATG GGACGCTGAT GCAGTATTTT   120

```
GAATGGTACA TGCCCAATGA CGGCCAACAT TGGAAGCGTT TGCAAAACGA CTCGGCATAT      180

TTGGCTGAAC ACGGTATTAC TGCCGTCTGG ATTCCCCCGG CATATAAGGG AACGAGCCAA      240

GCGGATGTGG GCTACGGTGC TTACGACCTT TATGATTTAG GGGAGTTTCA TCAAAAAGGG      300

ACGGTTCGGA CAAAGTACGG CACAAAAGGA GAGCTGCAAT CTGCGATCAA AGTCTTCAT      360

TCCCGCGACA TTAACGTTTA CGGGGATGTG GTCATCAACC ACAAAGGCGG CGCTGATGCG      420

ACCGAAGATG TAACCGCGGT TGAAGTCGAT CCCGCTGACC GCAACCGCGT AATCTCAGGA      480

GAACACCTAA TTAAAGCCTG GACACATTTT CATTTTCCGG GGGCCGGCAG CACATACAGC      540

GATTTTAAAT GGCATTGGTA CCATTTTGAC GGAACCGATT GGGACGAGTC CCGAAAGCTG      600

AACCGCATCT ATAAGTTTCA AGGAAAGGCT TGGGATTGGG AAGTTTCCAA TGAAAACGGC      660

AACTATGATT ATTTGATGTA TGCCGACATC GATTATGACC ATCCTGATGT CGCAGCAGAA      720

ATTAAGAGAT GGGGCACTTG GTATGCCAAT GAACTGCAAT GGACGGAAA CCGTCTTGAT      780

GCTGTCAAAC ACATTAAATT TTCTTTTTTG CGGGATTGGG TTAATCATGT CAGGGAAAAA      840

ACGGGGAAGG AAATGTTTAC GGTAGCTGAA TATTGGCAGA ATGACTTGGG CGCGCTGGAA      900

AACTATTTGA CAAAAACAAA TTTTAATCAT TCAGTGTTTG ACGTGCCGCT TCATTATCAG      960

TTCCATGCTG CATCGACACA GGGAGGCGGC TATGATATGA GGAAATTGCT GAACGGTACG     1020

GTCGTTTCCA AGCATCCGTT GAAATCGGTT ACATTTGTCG ATAACCATGA TACACAGCCG     1080

GGGCAATCGC TTGAGTCGAC TGTCCAAACA TGGTTTAAGC CGCTTGCTTA CGCTTTTATT     1140

CTCACAAGGG AATCTGGATA CCCTCAGGTT TTCTACGGGG ATATGTACGG GACGAAAGGA     1200

GACTCCCAGC GCGAAATTCC TGCCTTGAAA CACAAAATTG AACCGATCTT AAAAGCGAGA     1260

AAACAGTATG CGTACGGAGC ACAGCATGAT TATTTCGACC ACCATGACAT TGTCGGCTGG     1320

ACAAGGGAAG GCGACAGCTC GGTTGCAAAT TCAGGTTTGG CGGCATTAAT AACAGACGGA     1380

CCCGGTGGGG CAAAGCGAAT GTATGTCGGC CGGCAAAACG CCGGTGAGAC ATGGCATGAC     1440

ATTACCGGAA ACCGTTCGGA GCCGGTTGTC ATCAATTCGG AAGGCTGGGG AGAGTTTCAC     1500

GTAAACGGCG GATCCGTTTC AATTTATGTT CAAAGATCTC CTGGAGAGTA TCCAGCATGG     1560

GATCCAAATC AAATTTACAC AAATGAAATT GTGTACCATA ACGGCCAGCT ATGGCAAGCA     1620

AAATGGTGGA CACAAAATCA AGAGCCAGGT GACCCGTACG GTCCGTGGGA ACCACTCAAT     1680

TAA                                                                  1683
```

(2) INFORMATION FOR SEQ ID NO: 6:

(i) SEQUENCE CHARACTERISTICS:
        (A) LENGTH: 560 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 6:

```
Met Lys Gln Gln Lys Arg Leu Tyr Ala Arg Leu Leu Thr Leu Leu Phe
 1               5                  10                  15

Ala Leu Ile Phe Leu Leu Pro His Ser Ala Ala Ala Ala Asn Leu
                20                  25                  30

Asn Gly Thr Leu Met Gln Tyr Phe Glu Trp Tyr Met Pro Asn Asp Gly
            35                  40                  45

Gln His Trp Lys Arg Leu Gln Asn Asp Ser Ala Tyr Leu Ala Glu His
        50                  55                  60

Gly Ile Thr Ala Val Trp Ile Pro Pro Ala Tyr Lys Gly Thr Ser Gln
```

```
               65                  70                  75                  80
Ala Asp Val Gly Tyr Gly Ala Tyr Asp Leu Tyr Asp Leu Gly Glu Phe
                            85                  90                  95

His Gln Lys Gly Thr Val Arg Thr Lys Tyr Gly Thr Lys Gly Glu Leu
            100                 105                 110

Gln Ser Ala Ile Lys Ser Leu His Ser Arg Asp Ile Asn Val Tyr Gly
            115                 120                 125

Asp Val Val Ile Asn His Lys Gly Gly Ala Asp Ala Thr Glu Asp Val
            130                 135                 140

Thr Ala Val Glu Val Asp Pro Ala Asp Arg Asn Arg Val Ile Ser Gly
145                 150                 155                 160

Glu His Leu Ile Lys Ala Trp Thr His Phe His Phe Pro Gly Ala Gly
                165                 170                 175

Ser Thr Tyr Ser Asp Phe Lys Trp His Trp Tyr His Phe Asp Gly Thr
                180                 185                 190

Asp Trp Asp Glu Ser Arg Lys Leu Asn Arg Ile Tyr Lys Phe Gln Gly
            195                 200                 205

Lys Ala Trp Asp Trp Glu Val Ser Asn Glu Asn Gly Asn Tyr Asp Tyr
            210                 215                 220

Leu Met Tyr Ala Asp Ile Asp Tyr Asp His Pro Asp Val Ala Ala Glu
225                 230                 235                 240

Ile Lys Arg Trp Gly Thr Trp Tyr Ala Asn Glu Leu Gln Leu Asp Gly
                245                 250                 255

Asn Arg Leu Asp Ala Val Lys His Ile Lys Phe Ser Phe Leu Arg Asp
            260                 265                 270

Trp Val Asn His Val Arg Glu Lys Thr Gly Lys Glu Met Phe Thr Val
            275                 280                 285

Ala Glu Tyr Trp Gln Asn Asp Leu Gly Ala Leu Glu Asn Tyr Leu Asn
            290                 295                 300

Lys Thr Asn Phe Asn His Ser Val Phe Asp Val Pro Leu His Tyr Gln
305                 310                 315                 320

Phe His Ala Ala Ser Thr Gln Gly Gly Gly Tyr Asp Met Arg Lys Leu
                325                 330                 335

Leu Asn Gly Thr Val Val Ser Lys His Pro Leu Lys Ser Val Thr Phe
                340                 345                 350

Val Asp Asn His Asp Thr Gln Pro Gly Gln Ser Leu Glu Ser Thr Val
            355                 360                 365

Gln Thr Trp Phe Lys Pro Leu Ala Tyr Ala Phe Ile Leu Thr Arg Glu
            370                 375                 380

Ser Gly Tyr Pro Gln Val Phe Tyr Gly Asp Met Tyr Gly Thr Lys Gly
385                 390                 395                 400

Asp Ser Gln Arg Glu Ile Pro Ala Leu Lys His Lys Ile Glu Pro Ile
            405                 410                 415

Leu Lys Ala Arg Lys Gln Tyr Ala Tyr Gly Ala Gln His Asp Tyr Phe
            420                 425                 430

Asp His His Asp Ile Val Gly Trp Thr Arg Glu Gly Asp Ser Ser Val
            435                 440                 445

Ala Asn Ser Gly Leu Ala Ala Leu Ile Thr Asp Gly Pro Gly Gly Ala
            450                 455                 460

Lys Arg Met Tyr Val Gly Arg Gln Asn Ala Gly Glu Thr Trp His Asp
465                 470                 475                 480

Ile Thr Gly Asn Arg Ser Glu Pro Val Val Ile Asn Ser Glu Gly Trp
                485                 490                 495
```

```
Gly Glu Phe His Val Asn Gly Gly Ser Val Ser Ile Tyr Val Gln Arg
            500                 505                 510

Ser Pro Gly Glu Tyr Pro Ala Trp Asp Pro Asn Gln Ile Tyr Thr Asn
            515                 520                 525

Glu Ile Val Tyr His Asn Gly Gln Leu Trp Gln Ala Lys Trp Trp Thr
    530                 535                 540

Gln Asn Gln Glu Pro Gly Asp Pro Tyr Gly Pro Trp Glu Pro Leu Asn
545                 550                 555                 560

(2) INFORMATION FOR SEQ ID NO:7:

(i) SEQUENCE CHARACTERISTICS:
        (A) LENGTH: 1893 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:7:
```

| | |
|---|---|
| ATGAAACAAC AAAAACGGCT TTACGCCCGA TTGCTGACGC TGTTATTTGC GCTCATCTTC | 60 |
| TTGCTGCCTC ATTCTGCAGC AGCGGCGGCA AATCTTAATG CTCCCGGCTG CCGCGTCGAC | 120 |
| TACGCCGTCA CCAACCAGTG GCCCGGCGGC TTCGGCGCCA ACGTCACGAT CACCAACCTC | 180 |
| GGCGACCCCG TCTCGTCGTG GAAGCTCGAC TGGACCTACA CCGCAGGCCA GCGGATCCAG | 240 |
| CAGCTGTGGA ACGGCACCGC GTCGACCAAC GGCGGCCAGG TCTCCGTCAC CAGCCTGCCC | 300 |
| TGGAACGGCA GCATCCCGAC CGGCGGCACG GCGTCGTTCG GGTTCAACGG CTCGTGGGCC | 360 |
| GGGTCCAACC CGACGCCGGC GTCGTTCTCG CTCAACGGCA CCACGTGCAC TGGTACAGTT | 420 |
| CCTACAACTA GTCCTACACG TGCAAATCTT AATGGACGC TGATGCAGTA TTTTGAATGG | 480 |
| TACATGCCCA ATGACGGCCA ACATTGGAGG CGTTTGCAAA ACGACTCGGC ATATTTGGCT | 540 |
| GAACACGGTA TTACTGCCGT CTGGATTCCC CCGGCATATA AGGGAACGAG CCAAGCGGAT | 600 |
| GTGGGCTACG GTGCTTACGA CCTTTATGAT TTAGGGGAGT TTCATCAAAA AGGGACGGTT | 660 |
| CGGACAAAGT ACGGCACAAA AGGAGAGCTG CAATCTGCGA TCAAAAGTCT TCATTCCCGC | 720 |
| GACATTAACG TTTACGGGGA TGTGGTCATC AACCACAAAG GCGGCGCTGA TGCGACCGAA | 780 |
| GATGTAACCG CGGTTGAAGT CGATCCCGCT GACCGCAACC GCGTAATTTC AGGAGAACAC | 840 |
| CTAATTAAAG CCTGGACACA TTTTCATTTT CCGGGGCGCG GCAGCACATA CAGCGATTTT | 900 |
| AAATGGCATT GGTACCATTT TGACGGAACC GATTGGGACG AGTCCCGAAA GCTGAACCGC | 960 |
| ATCTATAAGT TCAAGGAAA GGCTTGGGAT TGGGAAGTTT CCAATGAAAA CGGCAACTAT | 1020 |
| GATTATTTGA TGTATGCCGA CATCGATTAT GACCATCCTG ATGTCGCAGC AGAAATTAAG | 1080 |
| AGATGGGGCA CTTGGTATGC CAATGAACTG CAATTGGACG GTTTCCGTCT TGATGCTGTC | 1140 |
| AAACACATTA AATTTTCTTT TTTGCGGGAT TGGGTTAATC ATGTCAGGGA AAAAACGGGG | 1200 |
| AAGGAAATGT TTACGGTAGC TGAATATTGG CAGAATGACT TGGGCGCGCT GGAAAACTAT | 1260 |
| TTGAACAAAA CAAATTTTAA TCATTCAGTG TTTGACGTGC CGCTTCATTA TCAGTTCCAT | 1320 |
| GCTGCATCGA CACAGGGAGG CGGCTATGAT ATGAGGAAAT TGCTGAACGG TACGGTCGTT | 1380 |
| TCCAAGCATC CGTTGAAATC GGTTACATTT GTCGATAACC ATGATACACA GCCGGGGCAA | 1440 |
| TCGCTTGAGT CGACTGTCCA AACATGGTTT AAGCCGCTTG CTTACGCTTT TATTCTCACA | 1500 |
| AGGGAATCTG GATACCCTCA GGTTTTCTAC GGGGATATGT ACGGGACGAA AGGAGACTCC | 1560 |
| CAGCGCGAAA TTCCTGCCTT GAAACACAAA ATTGAACCGA TCTTAAAAGC GAGAAAACAG | 1620 |
| TATGCGTACG GAGCACAGCA TGATTATTTC GACCACCATG ACATTGTCGG CTGGACAAGG | 1680 |

-continued

```
GAAGGCGACA GCTCGGTTGC AAATTCAGGT TTGGCGGCAT TAATAACAGA CGGACCCGGT    1740

GGGGCAAAGC GAATGTATGT CGGCCGGCAA AACGCCGGTG AGACATGGCA TGACATTACC    1800

GGAAACCGTT CGGAGCCGGT TGTCATCAAT TCGGAAGGCT GGGGAGAGTT TCACGTAAAC    1860

GGCGGGTCGG TTTCAATTTA TGTTCAAAGA TAG                                 1893
```

(2) INFORMATION FOR SEQ ID NO:8:

(i) SEQUENCE CHARACTERISTICS:
        (A) LENGTH: 631 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:8:

```
Met Lys Gln Gln Lys Arg Leu Tyr Ala Arg Leu Leu Thr Leu Leu Phe
 1               5                  10                  15

Ala Leu Ile Phe Leu Leu Pro His Ser Ala Ala Ala Ala Ala Asn Leu
                20                  25                  30

Asn Ala Pro Gly Cys Arg Val Asp Tyr Ala Val Thr Asn Gln Trp Pro
            35                  40                  45

Gly Gly Phe Gly Ala Asn Val Thr Ile Thr Asn Leu Gly Asp Pro Val
    50                  55                  60

Ser Ser Trp Lys Leu Asp Trp Thr Tyr Thr Ala Gly Gln Arg Ile Gln
65                  70                  75                  80

Gln Leu Trp Asn Gly Thr Ala Ser Thr Asn Gly Gln Val Ser Val
                85                  90                  95

Thr Ser Leu Pro Trp Asn Gly Ser Ile Pro Thr Gly Gly Thr Ala Ser
                100                 105                 110

Phe Gly Phe Asn Gly Ser Trp Ala Gly Ser Asn Pro Thr Pro Ala Ser
            115                 120                 125

Phe Ser Leu Asn Gly Thr Thr Cys Thr Gly Thr Val Pro Thr Thr Ser
    130                 135                 140

Pro Thr Arg Ala Asn Leu Asn Gly Thr Leu Met Gln Tyr Phe Glu Trp
145                 150                 155                 160

Tyr Met Pro Asn Asp Gly Gln His Trp Arg Arg Leu Gln Asn Asp Ser
                165                 170                 175

Ala Tyr Leu Ala Glu His Gly Ile Thr Ala Val Trp Ile Pro Pro Ala
            180                 185                 190

Tyr Lys Gly Thr Ser Gln Ala Asp Val Gly Tyr Gly Ala Tyr Asp Leu
    195                 200                 205

Tyr Asp Leu Gly Glu Phe His Gln Lys Gly Thr Val Arg Thr Lys Tyr
210                 215                 220

Gly Thr Lys Gly Glu Leu Gln Ser Ala Ile Lys Ser Leu His Ser Arg
225                 230                 235                 240

Asp Ile Asn Val Tyr Gly Asp Val Val Ile Asn His Lys Gly Gly Ala
                245                 250                 255

Asp Ala Thr Glu Asp Val Thr Ala Val Glu Val Asp Pro Ala Asp Arg
            260                 265                 270

Asn Arg Val Ile Ser Gly Glu His Leu Ile Lys Ala Trp Thr His Phe
    275                 280                 285

His Phe Pro Gly Arg Gly Ser Thr Tyr Ser Asp Phe Lys Trp His Trp
            290                 295                 300

Tyr His Phe Asp Gly Thr Asp Trp Asp Glu Ser Arg Lys Leu Asn Arg
```

```
305                 310                 315                 320
Ile Tyr Lys Phe Gln Gly Lys Ala Trp Asp Trp Glu Val Ser Asn Glu
                325                 330                 335

Asn Gly Asn Tyr Asp Tyr Leu Met Tyr Ala Asp Ile Asp Tyr Asp His
            340                 345                 350

Pro Asp Val Ala Ala Glu Ile Lys Arg Trp Gly Thr Trp Tyr Ala Asn
        355                 360                 365

Glu Leu Gln Leu Asp Gly Phe Arg Leu Asp Ala Val Lys His Ile Lys
    370                 375                 380

Phe Ser Phe Leu Arg Asp Trp Val Asn His Val Arg Glu Lys Thr Gly
385                 390                 395                 400

Lys Glu Met Phe Thr Val Ala Glu Tyr Trp Gln Asn Asp Leu Gly Ala
                405                 410                 415

Leu Glu Asn Tyr Leu Asn Lys Thr Asn Phe Asn His Ser Val Phe Asp
            420                 425                 430

Val Pro Leu His Tyr Gln Phe His Ala Ala Ser Thr Gln Gly Gly Gly
        435                 440                 445

Tyr Asp Met Arg Lys Leu Leu Asn Gly Thr Val Ser Lys His Pro
    450                 455                 460

Leu Lys Ser Val Thr Phe Val Asp Asn His Asp Thr Gln Pro Gly Gln
465                 470                 475                 480

Ser Leu Glu Ser Thr Val Gln Thr Trp Phe Lys Pro Leu Ala Tyr Ala
                485                 490                 495

Phe Ile Leu Thr Arg Glu Ser Gly Tyr Pro Gln Val Phe Tyr Gly Asp
            500                 505                 510

Met Tyr Gly Thr Lys Gly Asp Ser Gln Arg Glu Ile Pro Ala Leu Lys
        515                 520                 525

His Lys Ile Glu Pro Ile Leu Lys Ala Arg Lys Gln Tyr Ala Tyr Gly
    530                 535                 540

Ala Gln His Asp Tyr Phe Asp His His Asp Ile Val Gly Trp Thr Arg
545                 550                 555                 560

Glu Gly Asp Ser Ser Val Ala Asn Ser Gly Leu Ala Ala Leu Ile Thr
                565                 570                 575

Asp Gly Pro Gly Gly Ala Lys Arg Met Tyr Val Gly Arg Gln Asn Ala
            580                 585                 590

Gly Glu Thr Trp His Asp Ile Thr Gly Asn Arg Ser Glu Pro Val Val
        595                 600                 605

Ile Asn Ser Glu Gly Trp Gly Glu Phe His Val Asn Gly Gly Ser Val
    610                 615                 620

Ser Ile Tyr Val Gln Arg Glx
625                 630

(2) INFORMATION FOR SEQ ID NO:9:

(i) SEQUENCE CHARACTERISTICS:
        (A) LENGTH: 5679 base pairs
        (B) TYPE: nucleic acid
        (C) STRANDEDNESS: single
        (D) TOPOLOGY: linear (xi) SEQUENCE DESCRIPTION: SEQ ID NO:9:

GCGCCCAATA CGCAAACCGC CTCTCCCCGC GCGTTGGCCG ATTCATTAAT GCAGCTGGCA     60

CGACAGGTTT CCCGACTGGA AAGCGGGCAG TGAGCGCAAC GCAATTAATG TGAGTTAGCT    120

CACTCATTAG GCACCCCAGG CTTTACACTT TATGCTTCCG GCTCGTATGT TGTGTGGAAT    180

TGTGAGCGGA TAACAATTTC ACACAGGAAA CAGCTATGAC CATGATTACG CCAAGCTTGC    240
```

```
ATGCCTGCAG GTCGACGCAT TCCGAATACG AGGCCTGATT AATGATTACA TACGCCTCCG      300
GGTAGTAGAC CGAGCAGCCG AGCCAGTTCA GCGCCTAAAA CGCCTTATAC AATTAAGCAG      360
TTAAAGAAGT TAGAATCTAC GCTTAAAAAG CTACTTAAAA ATCGATCTCG CAGTCCCGAT      420
TCGCCTATCA AAACCAGTTT AAATCAACTG ATTAAAGGTG CCGAACGAGC TATAAATGAT      480
ATAACAATAT TAAAGCATTA ATTAGAGCAA TATCAGGCCG CGCACGAAAG GCAACTTAAA      540
AAGCGAAAGC GCTCTACTAA ACAGATTACT TTTGAAAAAG GCACATCAGT ATTTAAAGCC      600
CGAATCCTTA TTAAGCGCCG AAATCAGGCA GATAAAGCCA TACAGGCAGA TAGACCTCTA      660
CCTATTAAAT CGGCTTCTAG GCGCGCTCCA TCTAAATGTT CTGGCTGTGG TGTACAGGGG      720
CATAAAATTA CGCACTACCC GAATCGATAG AACTACTCAT TTTTATATAG AAGTCAGAAT      780
TCATAGTGTT TTGATCATTT TAAATTTTTA TATGGCGGGT GGTGGGCAAC TCGCTTGCGC      840
GGGCAACTCG CTTACCGATT ACGTTAGGGC TGATATTTAC GTGAAAATCG TCAAGGGATG      900
CAAGACCAAA GTAGTAAAAC CCCGGAAGTC AACAGCATCC AAGCCCAAGT CCTTCACGGA      960
GAAACCCCAG CGTCCACATC ACGAGCGAAG GACCACCTCT AGGCATCGGA CGCACCATCC     1020
AATTAGAAGC AGCAAAGCGA AACAGCCCAA GAAAAGGTC GGCCCGTCGG CCTTTTCTGC      1080
AACGCTGATC ACGGGCAGCG ATCCAACCAA CACCCTCCAG AGTGACTAGG GGCGGAAATT     1140
TAAAGGGATT AATTTCCACT CAACCACAAA TCACAGTCGT CCCCGGTATT GTCCTGCAGA     1200
ATGCAATTTA AACTCTTCTG CGAATCGCTT GGATTCCCCG CCCCTAGTCG TAGAGCTTAA     1260
AGTATGTCCC TTGTCGATGC GATGATACAC AACATATAAA TACTAGCAAG GGATGCCATG     1320
CTTGGAGGAT AGCAACCGAC AACATCACAT CAAGCTCTCC CTTCTCTGAA CAATAAACCC     1380
CACAGGGGGG ATCCACTAGT AACGGCCGCC AGTGTGCTGG AAAGCGACTT GAAACGCCCC     1440
AAATGAAGTC CTCCATCCTC GCCAGCGTCT TCGCCACGGG CGCCGTGGCT CAAAGTGGTC     1500
CGTGGCAGCA ATGTGGTGGC ATCGGATGGC AAGGATCGAC CGACTGTGTG TCGGGCTACC     1560
ACTGCGTCTA CCAGAACGAT TGGTACAGCC AGTGCGTGCC TGGCGCGGCG TCGACAACGC     1620
TGCAGACATC GACCACGTCC AGGCCCACCG CCACCAGCAC CGCCCCTCCG TCGTCCACCA     1680
CCTCGCCTAG CGTGGCCAGT CCTATTCGTC GAGAGGTCTC GCAGGATCTG TTTAACCAGT     1740
TCAATCTCTT TGCACAGTAT TCTGCAGCCG CATACTGCGG AAAAAACAAT GATGCCCCAG     1800
CTGGTACAAA CATTACGTGC ACGGGAAATG CCTGCCCCGA GGTAGAGAAG GCGGATGCAA     1860
CGTTTCTCTA CTCGTTTGAA GACTCTGGAG TGGGCGATGT CACCGGCTTC CTTGCTCTCG     1920
ACAACACGAA CAAATTGATC GTCCTCTCTT TCCGTGGCTC TCGTTCCATA GAGAACTGGA     1980
TCGGGAATCT TAAGTTCCTC TTGAAAAAAA TAAATGACAT TTGCTCCGGC TGCAGGGGAC     2040
ATGACGGCTT CACTTCGTCC TGGAGGTCTG TAGCCGATAC GTTAAGGCAG AAGGTGGAGG     2100
ATGCTGTGAG GGAGCATCCC GACTATCGCG TGGTGTTTAC CGGACATAGC TTGGGTGGTG     2160
CATTGGCAAC TGTTGCCGGA GCAGACCTGC GTGGAAATGG GTATGATATC GACGTGTTTT     2220
CATATGGCGC CCCCCGAGTC GGAAACAGGG CTTTTGCAGA ATTCCTGACC GTACAGACCG     2280
GCGGAACACT CTACCGCATT ACCCACACCA ATGATATTGT CCCTAGACTC CCGCCGCGCG     2340
AATTCGGTTA CAGCCATTCT AGCCCAGAAT ACTGGATCAA ATCTGGAACC CTTGTCCCCG     2400
TCACCCGAAA CGATATCGTG AAGATAGAAG GCATCGATGC CACCGGCGGC AATAACCGGC     2460
CGAACATTCC GGATATCCCT GCGCACCTAT GGTACTTCGG GTTAATTGGG ACATGTCTTT     2520
AGTGGCCGGC GCGGCTGGGT CGACTCTAGC GAGCTCGAGA TCTAGAGGGT GACTGACACC     2580
TGGCGGTAGA CAATCAATCC ATTTCGCTAT AGTTAAAGGA TGGGGATGAG GGCAATTGGT     2640
```

```
TATATGATCA TGTATGTAGT GGGTGTGCAT AATAGTAGTG AAATGGAAGC CAAGTCATGT    2700

GATTGTAATC GACCGACGGA ATTGAGGATA TCCGGAAATA CAGACACCGT GAAAGCCATG    2760

GTCTTTCCTT CGTGTAGAAG ACCAGACAGA CAGTCCCTGA TTTACCCTTG CACAAAGCAC    2820

TAGAAAATTA GCATTCCATC CTTCTCTGCT TGCTCTGCTG ATATCACTGT CATTCAATGC    2880

ATAGCCATGA GCTCATCTTA GATCCAAGCA CGTAATTCCA TAGCCGAGGT CCACAGTGGA    2940

GCAGCAACAT TCCCCATCAT TGCTTTCCCC AGGGGCCTCC CAACGACTAA ATCAAGAGTA    3000

TATCTCTACC GTCCAATAGA TCGTCTTCGC TTCAAAATCT TTGACAATTC AAGAGGGTC     3060

CCCATCCATC AAACCCAGTT CAATAATAGC CGAGATGCAT GGTGGAGTCA ATTAGGCAGT    3120

ATTGCTGGAA TGTCGGGCCA GTTGGCCCGG GTGGTCATTG GCCGCCTGTG ATGCCATCTG    3180

CCACTAAATC CGATCATTGA TCCACCGCCC ACGAGGCGCG TCTTTGCTTT TTGCGCGGCG    3240

TCCAGGTTCA ACTCTCTCGC TCTAGATATC GATGAATTCA CTGGCCGTCG TTTTACAACG    3300

TCGTGACTGG GAAAACCCTG GCGTTACCCA ACTTAATCGC CTTGCAGCAC ATCCCCCTTT    3360

CGCCAGCTGG CGTAATAGCG AAGAGGCCCG CACCGATCGC CCTTCCCAAC AGTTGCGCAG    3420

CCTGAATGGC GAATGGCGCC TGATGCGGTA TTTTCTCCTT ACGCATCTGT GCGGTATTTC    3480

ACACCGCATA TGGTGCACTC TCAGTACAAT CTGCTCTGAT GCCGCATAGT TAAGCCAGCC    3540

CCGACACCCG CCAACACCCG CTGACGCGCC CTGACGGGCT TGTCTGCTCC CGGCATCCGC    3600

TTACAGACAA GCTGTGACCG TCTCCGGGAG CTGCATGTGT CAGAGGTTTT CACCGTCATC    3660

ACCGAAACGC GCGAGACGAA AGGGCCTCGT GATACGCCTA TTTTTATAGG TTAATGTCAT    3720

GATAATAATG GTTTCTTAGA CGTCAGGTGG CACTTTTCGG GGAAATGTGC GCGGAACCCC    3780

TATTTGTTTA TTTTTCTAAA TACATTCAAA TATGTATCCG CTCATGAGAC AATAACCCTG    3840

ATAAATGCTT CAATAATATT GAAAAAGGAA GAGTATGAGT ATTCAACATT TCCGTGTCGC    3900

CCTTATTCCC TTTTTTGCGG CATTTTGCCT TCCTGTTTTT GCTCACCCAG AAACGCTGGT    3960

GAAAGTAAAA GATGCTGAAG ATCAGTTGGG TGCACGAGTG GGTTACATCG AACTGGATCT    4020

CAACAGCGGT AAGATCCTTG AGAGTTTTCG CCCCGAAGAA CGTTTTCCAA TGATGAGCAC    4080

TTTTAAAGTT CTGCTATGTG GCGCGGTATT ATCCCGTATT GACGCCGGGC AAGAGCAACT    4140

CGGTCGCCGC ATACACTATT CTCAGAATGA CTTGGTTGAC GCGTCACCAG TCACAGAAAA    4200

GCATCTTACG GATGGCATGA CAGTAAGAGA ATTATGCAGT GCTGCCATAA CCATGAGTGA    4260

TAACACTGCG GCCAACTTAC TTCTGACAAC GATCGGAGGA CCGAAGGAGC TAACCGCTTT    4320

TTTGCACAAC ATGGGGGATC ATGTAACTCG CCTTGATCGT TGGGAACCGG AGCTGAATGA    4380

AGCCATACCA AACGACGAGC GTGACACCAC GATGCCTGTA GCAATGGCAA CAACGTTGCG    4440

CAAACTATTA ACTGGCGAAC TACTTACTCT AGCTTCCCGG CAACAATTAA TAGACTGGAT    4500

GGAGGCGGAT AAAGTTGCAG GACCACTTCT GCGCTCGGCC CTTCCGGCTG GCTGGTTTAT    4560

TGCTGATAAA TCTGGAGCCG GTGAGCGTGG GTCTCGCGGT ATCATTGCAG CACTGGGGCC    4620

AGATGGTAAG CCCTCCCGTA TCGTAGTTAT CTACACGACG GGGAGTCAGG CAACTATGGA    4680

TGAACGAAAT AGACAGATCG CTGAGATAGG TGCCTCACTG ATTAAGCATT GGTAACTGTC    4740

AGACCAAGTT TACTCATATA TACTTTAGAT TGATTTAAAA CTTCATTTTT AATTTAAAAG    4800

GATCTAGGTG AAGATCCTTT TTGATAATCT CATGACCAAA ATCCCTTAAC GTGAGTTTTC    4860

GTTCCACTGA GCGTCAGACC CCGTAGAAAA GATCAAAGGA TCTTCTTGAG ATCCTTTTTT    4920

TCTGCGCGTA ATCTGCTGCT TGCAAACAAA AAAACCACCG CTACCAGCGG TGGTTTGTTT    4980

GCCGGATCAA GAGCTACCAA CTCTTTTTCC GAAGGTAACT GGCTTCAGCA GAGCGCAGAT    5040
```

| | |
|---|---|
| ACCAAATACT GTCCTTCTAG TGTAGCCGTA GTTAGGCCAC CACTTCAAGA ACTCTGTAGC | 5100 |
| ACCGCCTACA TACCTCGCTC TGCTAATCCT GTTACCAGTG GCTGCTGCCA GTGGCGATAA | 5160 |
| GTCGTGTCTT ACCGGGTTGG ACTCAAGACG ATAGTTACCG GATAAGGCGC AGCGGTCGGG | 5220 |
| CTGAACGGGG GGTTCGTGCA CACAGCCCAG CTTGGAGCGA ACGACCTACA CCGAACTGAG | 5280 |
| ATACCTACAG CGTGAGCTAT GAGAAAGCGC CACGCTTCCC GAAGGGAGAA AGGCGGACAG | 5340 |
| GTATCCGGTA AGCGGCAGGG TCGGAACAGG AGAGCGCACG AGGGAGCTTC CAGGGGGAAA | 5400 |
| CGCCTGGTAT CTTTATAGTC CTGTCGGGTT TCGCCACCTC TGACTTGAGC GTCGATTTTT | 5460 |
| GTGATGCTCG TCAGGGGGGC GGAGCCTATG GAAAAACGCC AGCAACGCGG CCTTTTTACG | 5520 |
| GTTCCTGGCC TTTTGCTGGC CTTTTGCTCA CATGTTCTTT CCTGCGTTAT CCCCTGATTC | 5580 |
| TGTGGATAAC CGTATTACCG CCTTTGAGTG AGCTGATACC GCTCGCCGCA GCCGAACGAC | 5640 |
| CGAGCGCAGC GAGTCAGTGA GCGAGGAAGC GGAAGAGAG | 5679 |

(2) INFORMATION FOR SEQ ID NO:10:

(i) SEQUENCE CHARACTERISTICS:
        (A) LENGTH: 5580 base pairs
        (B) TYPE: nucleic acid
        (C) STRANDEDNESS: single
        (D) TOPOLOGY: linear (xi) SEQUENCE DESCRIPTION: SEQ ID NO:10:

| | |
|---|---|
| GCGCCCAATA CGCAAACCGC CTCTCCCCGC GCGTTGGCCG ATTCATTAAT GCAGCTGGCA | 60 |
| CGACAGGTTT CCCGACTGGA AAGCGGGCAG TGAGCGCAAC GCAATTAATG TGAGTTAGCT | 120 |
| CACTCATTAG GCACCCCAGG CTTTACACTT TATGCTTCCG GCTCGTATGT TGTGTGGAAT | 180 |
| TGTGAGCGGA TAACAATTTC ACACAGGAAA CAGCTATGAC CATGATTACG CCAAGCTTGC | 240 |
| ATGCCTGCAG GTCGACGCAT TCCGAATACG AGGCCTGATT AATGATTACA TACGCCTCCG | 300 |
| GGTAGTAGAC CGAGCAGCCG AGCCAGTTCA GCGCCTAAAA CGCCTTATAC AATTAAGCAG | 360 |
| TTAAAGAAGT TAGAATCTAC GCTTAAAAAG CTACTTAAAA ATCGATCTCG CAGTCCCGAT | 420 |
| TCGCCTATCA AAACCAGTTT AAATCAACTG ATTAAGGTG CCGAACGAGC TATAAATGAT | 480 |
| ATAACAATAT TAAAGCATTA ATTAGAGCAA TATCAGGCCG CGCACGAAAG GCAACTTAAA | 540 |
| AAGCGAAAGC GCTCTACTAA ACAGATTACT TTTGAAAAAG GCACATCAGT ATTTAAAGCC | 600 |
| CGAATCCTTA TTAAGCGCCG AAATCAGGCA GATAAAGCCA TACAGGCAGA TAGACCTCTA | 660 |
| CCTATTAAAT CGGCTTCTAG GCGCGCTCCA TCTAAATGTT CTGGCTGTGG TGTACAGGGG | 720 |
| CATAAAATTA CGCACTACCC GAATCGATAG AACTACTCAT TTTTATATAG AAGTCAGAAT | 780 |
| TCATAGTGTT TTGATCATTT TAAATTTTTA TATGGCGGGT GGTGGGCAAC TCGCTTGCGC | 840 |
| GGGCAACTCG CTTACCGATT ACGTTAGGGC TGATATTTAC GTGAAAATCG TCAAGGGATG | 900 |
| CAAGACCAAA GTAGTAAAAC CCCGGAAGTC AACAGCATCC AAGCCCAAGT CCTTCACGGA | 960 |
| GAAACCCCAG CGTCCACATC ACGAGCGAAG GACCACCTCT AGGCATCGGA CGCACCATCC | 1020 |
| AATTAGAAGC AGCAAAGCGA AACAGCCCAA GAAAAAGGTC GGCCCGTCGG CCTTTTCTGC | 1080 |
| AACGCTGATC ACGGGCAGCG ATCCAACCAA CACCCTCCAG AGTGACTAGG GGCGGAAATT | 1140 |
| TAAAGGGATT AATTTCCACT CAACCACAAA TCACAGTCGT CCCCGGTATT GTCCTGCAGA | 1200 |
| ATGCAATTTA AACTCTTCTG CGAATCGCTT GGATTCCCCG CCCCTAGTCG TAGAGCTTAA | 1260 |
| AGTATGTCCC TTGTCGATGC GATGATACAC AACATATAAA TACTAGCAAG GGATGCCATG | 1320 |
| CTTGGAGGAT AGCAACCGAC AACATCACAT CAAGCTCTCC CTTCTCTGAA CAATAAACCC | 1380 |

```
CACAGGGGGG ATCCACTAGT AACGGCCGCC AGTGTGCTGG AAAGCGACTT GAAACGCCCC    1440

AAATGAAGTC CTCCATCCTC GCCAGCGTCT TCGCCACGGG CGCCGTGGCT CAAAGTGGTC    1500

CGTGGCAGCA ATGTGGTGGC ATCGGATGGC AAGGATCGAC CGACTGTGTG TCGGGCTACC    1560

ACTGCGTCTA CCAGAACGAT TGGTACAGCC AGTGCGCTAG CCCTCCTCGT CGACCTGTCT    1620

CGCAGGATCT GTTTAACCAG TTCAATCTCT TTGCACAGTA TTCTGCAGCC GCATACTGCG    1680

GAAAAAACAA TGATGCCCCA GCTGGTACAA ACATTACGTG CACGGGAAAT GCCTGCCCCG    1740

AGGTAGAGAA GGCGGATGCA ACGTTTCTCT ACTCGTTTGA AGACTCTGGA GTGGGCGATG    1800

TCACCGGCTT CCTTGCTCTC GACAACACGA ACAAATTGAT CGTCCTCTCT TTCCGTGGCT    1860

CTCGTTCCAT AGAGAACTGG ATCGGGAATC TTAAGTTCCT CTTGAAAAAA ATAAATGACA    1920

TTTGCTCCGG CTGCAGGGGA CATGACGGCT TCACTTCGTC CTGGAGGTCT GTAGCCGATA    1980

CGTTAAGGCA GAAGGTGGAG GATGCTGTGA GGGAGCATCC CGACTATCGC GTGGTGTTTA    2040

CCGGACATAG CTTGGGTGGT GCATTGGCAA CTGTTGCCGG AGCAGACCTG CGTGGAAATG    2100

GGTATGATAT CGACGTGTTT TCATATGGCG CCCCCCGAGT CGGAAACAGG GCTTTTGCAG    2160

AATTCCTGAC CGTACAGACC GGCGGAACAC TCTACCGCAT TACCCACACC AATGATATTG    2220

TCCCTAGACT CCCGCCGCGC GAATTCGGTT ACAGCCATTC TAGCCCAGAA TACTGGATCA    2280

AATCTGGAAC CCTTGTCCCC GTCACCCGAA ACGATATCGT GAAGATAGAA GGCATCGATG    2340

CCACCGGCGG CAATAACCGG CCGAACATTC CGGATATCCC TGCGCACCTA TGGTACTTCG    2400

GGTTAATTGG GACATGTCTT TAGTGGCCGG CGCGGCTGGG TCGACTCTAG CGAGCTCGAG    2460

ATCTAGAGGG TGACTGACAC CTGGCGGTAG ACAATCAATC CATTTCGCTA TAGTTAAAGG    2520

ATGGGGATGA GGGCAATTGG TTATATGATC ATGTATGTAG TGGGTGTGCA TAATAGTAGT    2580

GAAATGGAAG CCAAGTCATG TGATTGTAAT CGACCGACGG AATTGAGGAT ATCCGGAAAT    2640

ACAGACACCG TGAAAGCCAT GGTCTTTCCT TCGTGTAGAA GACCAGACAG ACAGTCCCTG    2700

ATTTACCCTT GCACAAAGCA CTAGAAAATT AGCATTCCAT CCTTCTCTGC TTGCTCTGCT    2760

GATATCACTG TCATTCAATG CATAGCCATG AGCTCATCTT AGATCCAAGC ACGTAATTCC    2820

ATAGCCGAGG TCCACAGTGG AGCAGCAACA TTCCCCATCA TTGCTTTCCC CAGGGGCCTC    2880

CCAACGACTA AATCAAGAGT ATATCTCTAC CGTCCAATAG ATCGTCTTCG CTTCAAAATC    2940

TTTGACAATT CCAAGAGGGT CCCCATCCAT CAAACCCAGT TCAATAATAG CCGAGATGCA    3000

TGGTGGAGTC AATTAGGCAG TATTGCTGGA ATGTCGGGCC AGTTGGCCCG GGTGGTCATT    3060

GGCCGCCTGT GATGCCATCT GCCACTAAAT CCGATCATTG ATCCACCGCC CACGAGGCGC    3120

GTCTTTGCTT TTTGCGCGGC GTCCAGGTTC AACTCTCTCG CTCTAGATAT CGATGAATTC    3180

ACTGGCCGTC GTTTTACAAC GTCGTGACTG GGAAAACCCT GGCGTTACCC AACTTAATCG    3240

CCTTGCAGCA CATCCCCCTT TCGCCAGCTG GCGTAATAGC GAAGAGGCCC GCACCGATCG    3300

CCCTTCCCAA CAGTTGCGCA GCCTGAATGG CGAATGGCGC CTGATGCGGT ATTTTCTCCT    3360

TACGCATCTG TGCGGTATTT CACACCGCAT ATGGTGCACT CTCAGTACAA TCTGCTCTGA    3420

TGCCGCATAG TTAAGCCAGC CCCGACACCC GCCAACACCC GCTGACGCGC CCTGACGGGC    3480

TTGTCTGCTC CCGGCATCCG CTTACAGACA AGCTGTGACC GTCTCCGGGA GCTGCATGTG    3540

TCAGAGGTTT TCACCGTCAT CACCGAAACG CGCGAGACGA AAGGGCCTCG TGATACGCCT    3600

ATTTTTATAG GTTAATGTCA TGATAATAAT GGTTTCTTAG ACGTCAGGTG GCACTTTTCG    3660

GGGAAATGTG CGCGGAACCC CTATTTGTTT ATTTTTCTAA ATACATTCAA ATATGTATCC    3720

GCTCATGAGA CAATAACCCT GATAAATGCT TCAATAATAT TGAAAAAGGA AGAGTATGAG    3780
```

```
TATTCAACAT TTCCGTGTCG CCCTTATTCC CTTTTTTGCG GCATTTTGCC TTCCTGTTTT      3840

TGCTCACCCA GAAACGCTGG TGAAAGTAAA AGATGCTGAA GATCAGTTGG GTGCACGAGT      3900

GGGTTACATC GAACTGGATC TCAACAGCGG TAAGATCCTT GAGAGTTTTC GCCCCGAAGA      3960

ACGTTTTCCA ATGATGAGCA CTTTTAAAGT TCTGCTATGT GGCGCGGTAT TATCCCGTAT      4020

TGACGCCGGG CAAGAGCAAC TCGGTCGCCG CATACACTAT TCTCAGAATG ACTTGGTTGA      4080

CGCGTCACCA GTCACAGAAA AGCATCTTAC GGATGGCATG ACAGTAAGAG AATTATGCAG      4140

TGCTGCCATA ACCATGAGTG ATAACACTGC GGCCAACTTA CTTCTGACAA CGATCGGAGG      4200

ACCGAAGGAG CTAACCGCTT TTTTGCACAA CATGGGGGAT CATGTAACTC GCCTTGATCG      4260

TTGGGAACCG GAGCTGAATG AAGCCATACC AAACGACGAG CGTGACACCA CGATGCCTGT      4320

AGCAATGGCA ACAACGTTGC GCAAACTATT AACTGGCGAA CTACTTACTC TAGCTTCCCG      4380

GCAACAATTA ATAGACTGGA TGGAGGCGGA TAAAGTTGCA GGACCACTTC TGCGCTCGGC      4440

CCTTCCGGCT GGCTGGTTTA TTGCTGATAA ATCTGGAGCC GGTGAGCGTG GGTCTCGCGG      4500

TATCATTGCA GCACTGGGGC CAGATGGTAA GCCCTCCCGT ATCGTAGTTA TCTACACGAC      4560

GGGGAGTCAG GCAACTATGG ATGAACGAAA TAGACAGATC GCTGAGATAG GTGCCTCACT      4620

GATTAAGCAT TGGTAACTGT CAGACCAAGT TTACTCATAT ATACTTTAGA TTGATTTAAA      4680

ACTTCATTTT TAATTTAAAA GGATCTAGGT GAAGATCCTT TTTGATAATC TCATGACCAA      4740

AATCCCTTAA CGTGAGTTTT CGTTCCACTG AGCGTCAGAC CCCGTAGAAA AGATCAAAGG      4800

ATCTTCTTGA GATCCTTTTT TTCTGCGCGT AATCTGCTGC TTGCAAACAA AAAAACCACC      4860

GCTACCAGCG GTGGTTTGTT TGCCGGATCA AGAGCTACCA ACTCTTTTTC CGAAGGTAAC      4920

TGGCTTCAGC AGAGCGCAGA TACCAAATAC TGTCCTTCTA GTGTAGCCGT AGTTAGGCCA      4980

CCACTTCAAG AACTCTGTAG CACCGCCTAC ATACCTCGCT CTGCTAATCC TGTTACCAGT      5040

GGCTGCTGCC AGTGGCGATA AGTCGTGTCT TACCGGGTTG GACTCAAGAC GATAGTTACC      5100

GGATAAGGCG CAGCGGTCGG GCTGAACGGG GGGTTCGTGC ACACAGCCCA GCTTGGAGCG      5160

AACGACCTAC ACCGAACTGA GATACCTACA GCGTGAGCTA TGAGAAAGCG CCACGCTTCC      5220

CGAAGGGAGA AAGGCGGACA GGTATCCGGT AAGCGGCAGG GTCGGAACAG GAGAGCGCAC      5280

GAGGGAGCTT CCAGGGGGAA ACGCCTGGTA TCTTTATAGT CCTGTCGGGT TTCGCCACCT      5340

CTGACTTGAG CGTCGATTTT TGTGATGCTC GTCAGGGGGG CGGAGCCTAT GGAAAAACGC      5400

CAGCAACGCG GCCTTTTTAC GGTTCCTGGC CTTTTGCTGG CCTTTTGCTC ACATGTTCTT      5460

TCCTGCGTTA TCCCCTGATT CTGTGGATAA CCGTATTACC GCCTTTGAGT GAGCTGATAC      5520

CGCTCGCCGC AGCCGAACGA CCGAGCGCAG CGAGTCAGTG AGCGAGGAAG CGGAAGAGAG      5580
```

(2) INFORMATION FOR SEQ ID NO:11:

(i) SEQUENCE CHARACTERISTICS:
        (A) LENGTH: 5697 base pairs
        (B) TYPE: nucleic acid
        (C) STRANDEDNESS: single
        (D) TOPOLOGY: linear (xi) SEQUENCE DESCRIPTION: SEQ ID NO:11:

```
GCGCCCAATA CGCAAACCGC CTCTCCCCGC GCGTTGGCCG ATTCATTAAT GCAGCTGGCA        60

CGACAGGTTT CCCGACTGGA AAGCGGGCAG TGAGCGCAAC GCAATTAATG TGAGTTAGCT       120

CACTCATTAG GCACCCCAGG CTTTACACTT TATGCTTCCG GCTCGTATGT TGTGTGGAAT       180

TGTGAGCGGA TAACAATTTC ACACAGGAAA CAGCTATGAC CATGATTACG CCAAGCTTGC       240

ATGCCTGCAG GTCGACGCAT TCCGAATACG AGGCCTGATT AATGATTACA TACGCCTCCG       300
```

```
GGTAGTAGAC CGAGCAGCCG AGCCAGTTCA GCGCCTAAAA CGCCTTATAC AATTAAGCAG      360

TTAAAGAAGT TAGAATCTAC GCTTAAAAAG CTACTTAAAA ATCGATCTCG CAGTCCCGAT      420

TCGCCTATCA AAACCAGTTT AAATCAACTG ATTAAAGGTG CCGAACGAGC TATAAATGAT      480

ATAACAATAT TAAAGCATTA ATTAGAGCAA TATCAGGCCG CGCACGAAAG GCAACTTAAA      540

AAGCGAAAGC GCTCTACTAA ACAGATTACT TTTGAAAAAG GCACATCAGT ATTTAAAGCC      600

CGAATCCTTA TTAAGCGCCG AAATCAGGCA GATAAAGCCA TACAGGCAGA TAGACCTCTA      660

CCTATTAAAT CGGCTTCTAG GCGCGCTCCA TCTAAATGTT CTGGCTGTGG TGTACAGGGG      720

CATAAAATTA CGCACTACCC GAATCGATAG AACTACTCAT TTTTATATAG AAGTCAGAAT      780

TCATAGTGTT TTGATCATTT TAAATTTTTA TATGGCGGGT GGTGGGCAAC TCGCTTGCGC      840

GGGCAACTCG CTTACCGATT ACGTTAGGGC TGATATTTAC GTGAAAATCG TCAAGGGATG      900

CAAGACCAAA GTAGTAAAAC CCCGGAAGTC AACAGCATCC AAGCCCAAGT CCTTCACGGA      960

GAAACCCCAG CGTCCACATC ACGAGCGAAG GACCACCTCT AGGCATCGGA CGCACCATCC     1020

AATTAGAAGC AGCAAAGCGA AACAGCCCAA GAAAAAGGTC GGCCCGTCGG CCTTTTCTGC     1080

AACGCTGATC ACGGGCAGCG ATCCAACCAA CACCCTCCAG AGTGACTAGG GGCGGAAATT     1140

TAAAGGGATT AATTTCCACT CAACCACAAA TCACAGTCGT CCCCGGTATT GTCCTGCAGA     1200

ATGCAATTTA AACTCTTCTG CGAATCGCTT GGATTCCCCG CCCCTAGTCG TAGAGCTTAA     1260

AGTATGTCCC TTGTCGATGC GATGATACAC AACATATAAA TACTAGCAAG GGATGCCATG     1320

CTTGGAGGAT AGCAACCGAC AACATCACAT CAAGCTCTCC CTTCTCTGAA CAATAAACCC     1380

CACAGGGGGG ATCCACTAGT AACGGCCGCC AGTGTGCTGG AAAGCGACTT GAAACGCCCC     1440

AAATGAAGTC CTCCATCCTC GCCAGCGTCT TCGCCACGGG CGCCGTGGCT CAAAGTGGTC     1500

CGTGGCAGCA ATGTGGTGGC ATCGGATGGC AAGGATCGAC CGACTGTGTG TCGGGCTACC     1560

ACTGCGTCTA CCAGAACGAT TGGTACAGCC AGTGCGCTAG CGTCCAGATC CCCTCCAGCA     1620

GCACCAGCTC TCCGGTCAAC CAGCCTACCA GCACCAGCAC CACGTCCACC TCCACCACCT     1680

CGAGCCCGCC AGTCCAGCCT ACGACTCCCA GCGCTAGCCC TCCTCGTCGA CCTGTCTCGC     1740

AGGATCTGTT TAACCAGTTC AATCTCTTTG CACAGTATTC TGCAGCCGCA TACTGCGGAA     1800

AAAACAATGA TGCCCCAGCT GGTACAAACA TTACGTGCAC GGGAAATGCC TGCCCCGAGG     1860

TAGAGAAGGC GGATGCAACG TTTCTCTACT CGTTTGAAGA CTCTGGAGTG GGCGATGTCA     1920

CCGGCTTCCT TGCTCTCGAC AACACGAACA AATTGATCGT CCTCTCTTTC CGTGGCTCTC     1980

GTTCCATAGA GAACTGGATC GGGAATCTTA AGTTCCTCTT GAAAAAAATA AATGACATTT     2040

GCTCCGGCTG CAGGGGACAT GACGGCTTCA CTTCGTCCTG GAGGTCTGTA GCCGATACGT     2100

TAAGGCAGAA GGTGGAGGAT GCTGTGAGGG AGCATCCCGA CTATCGCGTG GTGTTTACCG     2160

GACATAGCTT GGGTGGTGCA TTGGCAACTG TTGCCGGAGC AGACCTGCGT GGAAATGGGT     2220

ATGATATCGA CGTGTTTTCA TATGGCGCCC CCCGAGTCGG AAACAGGGCT TTTGCAGAAT     2280

TCCTGACCGT ACAGACCGGC GGAACACTCT ACCGCATTAC CCACACCAAT GATATTGTCC     2340

CTAGACTCCC GCCGCGCGAA TTCGGTTACA GCCATTCTAG CCCAGAATAC TGGATCAAAT     2400

CTGGAACCCT TGTCCCCGTC ACCCGAAACG ATATCGTGAA GATAGAAGGC ATCGATGCCA     2460

CCGGCGGCAA TAACCGGCCG AACATTCCGG ATATCCCTGC GCACCTATGG TACTTCGGGT     2520

TAATTGGGAC ATGTCTTTAG TGGCCGGCGC GGCTGGGTCG ACTCTAGCGA GCTCGAGATC     2580

TAGAGGGTGA CTGACACCTG GCGGTAGACA ATCAATCCAT TTCGCTATAG TTAAAGGATG     2640

GGGATGAGGG CAATTGGTTA TATGATCATG TATGTAGTGG GTGTGCATAA TAGTAGTGAA     2700
```

```
ATGGAAGCCA AGTCATGTGA TTGTAATCGA CCGACGGAAT TGAGGATATC CGGAAATACA    2760

GACACCGTGA AAGCCATGGT CTTTCCTTCG TGTAGAAGAC CAGACAGACA GTCCCTGATT    2820

TACCCTTGCA CAAAGCACTA GAAAATTAGC ATTCCATCCT TCTCTGCTTG CTCTGCTGAT    2880

ATCACTGTCA TTCAATGCAT AGCCATGAGC TCATCTTAGA TCCAAGCACG TAATTCCATA    2940

GCCGAGGTCC ACAGTGGAGC AGCAACATTC CCCATCATTG CTTTCCCCAG GGGCCTCCCA    3000

ACGACTAAAT CAAGAGTATA TCTCTACCGT CCAATAGATC GTCTTCGCTT CAAAATCTTT    3060

GACAATTCCA AGAGGGTCCC CATCCATCAA ACCCAGTTCA ATAATAGCCG AGATGCATGG    3120

TGGAGTCAAT TAGGCAGTAT TGCTGGAATG TCGGGCCAGT TGGCCCGGGT GGTCATTGGC    3180

CGCCTGTGAT GCCATCTGCC ACTAAATCCG ATCATTGATC CACCGCCCAC GAGGCGCGTC    3240

TTTGCTTTTT GCGCGGCGTC CAGGTTCAAC TCTCTCGCTC TAGATATCGA TGAATTCACT    3300

GGCCGTCGTT TTACAACGTC GTGACTGGGA AAACCCTGGC GTTACCCAAC TTAATCGCCT    3360

TGCAGCACAT CCCCCTTTCG CCAGCTGGCG TAATAGCGAA GAGGCCCGCA CCGATCGCCC    3420

TTCCCAACAG TTGCGCAGCC TGAATGGCGA ATGGCGCCTG ATGCGGTATT TTCTCCTTAC    3480

GCATCTGTGC GGTATTTCAC ACCGCATATG GTGCACTCTC AGTACAATCT GCTCTGATGC    3540

CGCATAGTTA AGCCAGCCCC GACACCCGCC AACACCCGCT GACGCGCCCT GACGGGCTTG    3600

TCTGCTCCCG GCATCCGCTT ACAGACAAGC TGTGACCGTC TCCGGGAGCT GCATGTGTCA    3660

GAGGTTTTCA CCGTCATCAC CGAAACGCGC GAGACGAAAG GCCTCGTGA TACGCCTATT    3720

TTTATAGGTT AATGTCATGA TAATAATGGT TTCTTAGACG TCAGGTGGCA CTTTTCGGGG    3780

AAATGTGCGC GGAACCCCTA TTTGTTTATT TTTCTAAATA CATTCAAATA TGTATCCGCT    3840

CATGAGACAA TAACCCTGAT AAATGCTTCA ATAATATTGA AAAAGGAAGA GTATGAGTAT    3900

TCAACATTTC CGTGTCGCCC TTATTCCCTT TTTTGCGGCA TTTTGCCTTC CTGTTTTTGC    3960

TCACCCAGAA ACGCTGGTGA AAGTAAAAGA TGCTGAAGAT CAGTTGGGTG CACGAGTGGG    4020

TTACATCGAA CTGGATCTCA ACAGCGGTAA GATCCTTGAG AGTTTTCGCC CCGAAGAACG    4080

TTTTCCAATG ATGAGCACTT TTAAAGTTCT GCTATGTGGC GCGGTATTAT CCCGTATTGA    4140

CGCCGGGCAA GAGCAACTCG GTCGCCGCAT ACACTATTCT CAGAATGACT TGGTTGACGC    4200

GTCACCAGTC ACAGAAAAGC ATCTTACGGA TGGCATGACA GTAAGAGAAT TATGCAGTGC    4260

TGCCATAACC ATGAGTGATA ACACTGCGGC CAACTTACTT CTGACAACGA TCGGAGGACC    4320

GAAGGAGCTA ACCGCTTTTT TGCACAACAT GGGGGATCAT GTAACTCGCC TTGATCGTTG    4380

GGAACCGGAG CTGAATGAAG CCATACCAAA CGACGAGCGT GACACCACGA TGCCTGTAGC    4440

AATGGCAACA ACGTTGCGCA AACTATTAAC TGGCGAACTA CTTACTCTAG CTTCCCGGCA    4500

ACAATTAATA GACTGGATGG AGGCGGATAA AGTTGCAGGA CCACTTCTGC GCTCGGCCCT    4560

TCCGGCTGGC TGGTTTATTG CTGATAAATC TGGAGCCGGT GAGCGTGGGT CTCGCGGTAT    4620

CATTGCAGCA CTGGGGCCAG ATGGTAAGCC CTCCCGTATC GTAGTTATCT ACACGACGGG    4680

GAGTCAGGCA ACTATGGATG AACGAAATAG ACAGATCGCT GAGATAGGTG CCTCACTGAT    4740

TAAGCATTGG TAACTGTCAG ACCAAGTTTA CTCATATATA CTTTAGATTG ATTTAAAACT    4800

TCATTTTTAA TTTAAAAGGA TCTAGGTGAA GATCCTTTTT GATAATCTCA TGACCAAAAT    4860

CCCTTAACGT GAGTTTTCGT TCCACTGAGC GTCAGACCCC GTAGAAAAGA TCAAAGGATC    4920

TTCTTGAGAT CCTTTTTTTC TGCGCGTAAT CTGCTGCTTG CAAACAAAAA AACCACCGCT    4980

ACCAGCGGTG GTTTGTTTGC CGGATCAAGA GCTACCAACT CTTTTTCCGA AGGTAACTGG    5040

CTTCAGCAGA GCGCAGATAC CAAATACTGT CCTTCTAGTG TAGCCGTAGT TAGGCCACCA    5100
```

```
CTTCAAGAAC TCTGTAGCAC CGCCTACATA CCTCGCTCTG CTAATCCTGT TACCAGTGGC    5160

TGCTGCCAGT GGCGATAAGT CGTGTCTTAC CGGGTTGGAC TCAAGACGAT AGTTACCGGA    5220

TAAGGCGCAG CGGTCGGGCT GAACGGGGGG TTCGTGCACA CAGCCCAGCT TGGAGCGAAC    5280

GACCTACACC GAACTGAGAT ACCTACAGCG TGAGCTATGA GAAAGCGCCA CGCTTCCCGA    5340

AGGGAGAAAG GCGGACAGGT ATCCGGTAAG CGGCAGGGTC GGAACAGGAG AGCGCACGAG    5400

GGAGCTTCCA GGGGGAAACG CCTGGTATCT TTATAGTCCT GTCGGGTTTC GCCACCTCTG    5460

ACTTGAGCGT CGATTTTTGT GATGCTCGTC AGGGGGGCGG AGCCTATGGA AAAACGCCAG    5520

CAACGCGGCC TTTTTACGGT TCCTGGCCTT TTGCTGGCCT TTTGCTCACA TGTTCTTTCC    5580

TGCGTTATCC CCTGATTCTG TGGATAACCG TATTACCGCC TTTGAGTGAG CTGATACCGC    5640

TCGCCGCAGC CGAACGACCG AGCGCAGCGA GTCAGTGAGC GAGGAAGCGG AAGAGAG      5697
```

(2) INFORMATION FOR SEQ ID NO:12:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (xi) SEQUENCE DESCRIPTION: SEQ ID NO:12:

```
GCTTTACGCC CGATTGCTGA CGCTG                                           25
```

(2) INFORMATION FOR SEQ ID NO:13:

(i) SEQUENCE CHARACTERISTICS:
        (A) LENGTH: 51 base pairs
        (B) TYPE: nucleic acid
        (C) STRANDEDNESS: single
        (D) TOPOLOGY: linear (xi) SEQUENCE DESCRIPTION: SEQ ID NO:13:

```
GCGATGAGAC GCGCGGCCGC CTATCTTTGA ACATAAATTG AAACGGATCC G              51
```

(2) INFORMATION FOR SEQ ID NO:14:

(i) SEQUENCE CHARACTERISTICS:
        (A) LENGTH: 68 base pairs
        (B) TYPE: nucleic acid
        (C) STRANDEDNESS: single
        (D) TOPOLOGY: linear (xi) SEQUENCE DESCRIPTION: SEQ ID NO:14:

```
GCTGCAGGAT CCGTTTCAAT TTATGTTCAA AGATCTGGCG GACCTGGAAC GCCAAATAAT    60

GGAAGAGG                                                              68
```

(2) INFORMATION FOR SEQ ID NO:15:

(i) SEQUENCE CHARACTERISTICS:
        (A) LENGTH: 46 base pairs
        (B) TYPE: nucleic acid
        (C) STRANDEDNESS: single
        (D) TOPOLOGY: linear (xi) SEQUENCE DESCRIPTION: SEQ ID NO:15:

```
GCACTAGCTA GACGGCCGCT ACCAGTCAAC ATTAACAGGA CCTGAG                    46
```

(2) INFORMATION FOR SEQ ID NO:16:

(i) SEQUENCE CHARACTERISTICS:
        (A) LENGTH: 71 base pairs (B) TYPE: nucleic acid
        (C) STRANDEDNESS: single
        (D) TOPOLOGY: linear (xi) SEQUENCE DESCRIPTION: SEQ ID NO:16:

GTAGGCTCAG TCATATGTTA CACATTGAAA GGGGAGGAGA ATCATGAAAA AGATAACTAC    60

TATTTTTGTC G    71

(2) INFORMATION FOR SEQ ID NO:17:

(i) SEQUENCE CHARACTERISTICS:
        (A) LENGTH: 51 base pairs
        (B) TYPE: nucleic acid
        (C) STRANDEDNESS: single
        (D) TOPOLOGY: linear (xi) SEQUENCE DESCRIPTION: SEQ ID NO:17:

GTACCTCGCG GGTACCAAGC GGCCGCTTAA TTGAGTGGTT CCCACGGACC G    51

(2) INFORMATION FOR SEQ ID NO:18:

(i) SEQUENCE CHARACTERISTICS:
        (A) LENGTH: 64 base pairs
        (B) TYPE: nucleic acid
        (C) STRANDEDNESS: single
        (D) TOPOLOGY: linear (xi) SEQUENCE DESCRIPTION: SEQ ID NO:18:

GCTGCAGGAT CCGTTTCAAT TTATGTTCAA AGATCTCCTG GAGAGTATCC AGCATGGGAC    60

CCAA    64

(2) INFORMATION FOR SEQ ID NO:19:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (xi) SEQUENCE DESCRIPTION: SEQ ID NO:19:

GCACAAGCTT GCGGCCGCTA ATTGAGTGGT TCCCACGGAC CG    42

(2) INFORMATION FOR SEQ ID NO:20:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:20:

CTCGTCCCAA TCGGTTCCGT C    21

(2) INFORMATION FOR SEQ ID NO:21:

(i) SEQUENCE CHARACTERISTICS:
        (A) LENGTH: 57 base pairs
        (B) TYPE: nucleic acid
        (C) STRANDEDNESS: single
        (D) TOPOLOGY: linear (xi) SEQUENCE DESCRIPTION: SEQ ID NO:21:

TGCACTGGTA CAGTTCCTAC AACTAGTCCT ACACGTGCAA ATCTTAATGG GACGCTG    57

(2) INFORMATION FOR SEQ ID NO:22:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (xi) SEQUENCE DESCRIPTION: SEQ ID NO:22:

CTGCCTCATT CTGCAGCAGC GGCGGCAAAT CTTAATGCTC CCGGCTGCCG CGTCGACTAC    60

(2) INFORMATION FOR SEQ ID NO:23:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (xi) SEQUENCE DESCRIPTION: SEQ ID NO:23:

TGTAGGAACT GTACCAGTGC ACGTGGTGCC GTTGAGC    37

(2) INFORMATION FOR SEQ ID NO:24:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:24:

ACGTAGTGGC CACGCTAGGC GAGGTGGTGG    30

(2) INFORMATION FOR SEQ ID NO:25:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:25:

CCACACTTCT CTTCCTTCCT C    21

(2) INFORMATION FOR SEQ ID NO:26:

(i) SEQUENCE CHARACTERISTICS:
        (A) LENGTH: 26 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:26:

Asn Asn Asn Pro Gln Gln Gly Asn Pro Asn Gln Gly Gly Asn Asn Gly
 1               5                  10                  15

Gly Gly Asn Gln Gly Gly Gly Asn Gly Gly
            20                  25

(2) INFORMATION FOR SEQ ID NO:27:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (xi) SEQUENCE DESCRIPTION: SEQ ID NO:27:

GATCTAGCTA GCAACAATAA CCCCCAGCAG GGCAACCCCA ACCAGGGCGG GAACAACGGC    60

(2) INFORMATION FOR SEQ ID NO:28:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:28:

GATCTAGCTA GCGCCGCCGT TGCCGCCGCC CTGGTTGCCG CCGCCGTTGT TCCCGCCCTG      60

(2) INFORMATION FOR SEQ ID NO:29:

(i) SEQUENCE CHARACTERISTICS:
        (A) LENGTH: 37 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:29:

Val Gln Ile Pro Ser Ser Ser Thr Ser Ser Pro Val Asn Gln Pro Thr
1               5                   10               15

Ser Thr Ser Thr Thr Ser Thr Ser Thr Thr Ser Ser Pro Pro Val Gln
           20                  25                30

Pro Thr Thr Pro Ser
       35

(2) INFORMATION FOR SEQ ID NO:30:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:30:

GATACTGCTA GCGTCCAGAT CCCCTCCAGC      30

(2) INFORMATION FOR SEQ ID NO:31:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:31:

GATACTGCTA GCGCTGGGAG TCGTAGGCTG      30

PROCESS AND COMPOSITION FOR DESIZING CELLULOSIC FABRIC WITH AN ENZYME HYBRID

CROSS-REFERENCE TO RELATED APPLICATIONS

This application is a continuation of application Ser. No. PCT/DK97/00041 filed Jan. 29, 1997 and claims priority under 35 U.S.C. 119 of Danish application serial no. 0093/96 filed Jan. 29, 1996, the contents of which are fully incorporated herein by reference.

FIELD OF THE INVENTION

The present invention relates to an improved enzymatic process for desizing [i.e. removing "size" (vide infra) from] fabric or textile, more particularly cellulose-containing fabric or textile, and to a composition for use in the process.

BACKGROUND OF THE INVENTION

During the weaving of textiles, the threads are exposed to considerable mechanical strain. In order to prevent breaking, they are usually reinforced by coating ("sizing") with a gelatinous substance ("size").

The most common sizing agent is starch in native or modified form. However, other polymeric substances, for example poly-vinylalcohol (PVA), polyvinylpyrrolidone (PVP), polyacrylic acid (PAA) or derivatives of cellulose [e.g. carboxy-methylcellulose (CMC), hydroxyethylcellulose, hydroxypropyl-cellulose or methylcellulose] may also be abundant in the size. Small amounts of, e.g., fats or oils may also be added to the size as a lubricant.

As a consequence of the presence of the size, the threads of the fabric are not able to absorb water, finishing agents or other compositions (e.g. bleaching, dyeing or crease-proofing compositions) to a sufficient degree. Uniform and durable finishing of the fabric can thus be achieved only after removal of the size from the fabric; a process of removing size for this purpose is known as a "desizing" process.

In cases where the size comprises a starch, the desizing treatment may be carried out using a starch-degrading enzyme (e.g. an amylase). In cases where the size comprises fat and/or oil, the desizing treatment may comprise the use of a lipolytic enzyme (a lipase). In cases where the size comprises a significant amount of carboxymethylcellulose (CMC) or other cellulose-derivatives, the desizing treatment may be carried out with a cellulolytic enzyme, either alone or in combination with other substances, optionally in combination with other enzymes, such as amylases and/or lipases.

It is an object of the present invention to achieve improved enzyme performance under desizing conditions by modifying the enzyme so as to alter (increase) the affinity of the enzyme for cellulosic fabric, whereby the modified enzyme comes into closer contact with the sizing agent in question.

SUMMARY OF THE INVENTION

It has now surprisingly been found possible to achieve improved enzymatic removal of a sizing agent present on cellulose-containing fabric or textile by means of an enzymatic process wherein the fabric or textile is contacted with an enzyme which has been modified so as to have increased affinity (relative to the unmodified enzyme) for binding to a cellulosic fabric or textile.

DETAILED DESCRIPTION OF THE INVENTION

The present invention thus relates, inter alia, to a process for desizing cellulosic fabric or textile, wherein the fabric or textile is treated (normally contacted in aqueous medium) with a modified enzyme (enzyme hybrid) which comprises a catalytically (enzymatically) active amino acid sequence of an enzyme, in particular of a non-cellulolytic enzyme, linked to an amino acid sequence comprising a cellulose-binding domain.

The term "desizing" is intended to be understood in a conventional manner, i.e. the removal of a sizing agent from the fabric.

The terms "cellulose-containing" and "cellulosic" when used herein in connection with fabric or textile are intended to indicate any type of fabric, in particular woven fabric, prepared from a cellulose-containing material, such as cotton, or from a cellulose-derived material (prepared, e.g., from wood pulp or from cotton).

In the present context, the term "fabric" is intended to include garments and other types of processed fabrics, and is used interchangeably with the term "textile".

Examples of cellulosic fabric manufactured from naturally occurring cellulosic fibre are cotton, ramie, jute and flax (linen) fabrics. Examples of cellulosic fabrics made from man-made cellulosic fibre are viscose (rayon) and lyocell (e.g. Tencel™) fabric; also of relevance in the context of the invention are all blends of cellulosic fibres (such as viscose, lyocell, cotton, ramie, jute or flax) with other fibres, such as wool, polyester, polyacrylic, polyamide or polyacetate fibres. Specific examples of blended cellulosic fabric are viscose/cotton blends, lyocell/cotton blends (e.g. Tencel™/cotton blends), viscose/wool blends, lyocell/wool blends, cotton/wool blends, cotton/polyester blends, viscose/cotton/polyester blends, wool/cotton/polyester blends, and flax/cotton blends.

Cellulose-binding Domains

Although a number of types of carbohydrate-binding domains have been described in the patent and scientific literature, the majority thereof—many of which derive from cellulolytic enzymes (cellulases)—are commonly referred to as "cellulose-binding domains"; a typical cellulose-binding domain (CBD) will thus be one which occurs in a cellulase and which binds preferentially to cellulose and/or to poly- or oligosaccharide fragments thereof.

Cellulose-binding (and other carbohydrate-binding) domains are polypeptide amino acid sequences which occur as integral parts of large polypeptides or proteins consisting of two or more polypeptide amino acid sequence regions, especially in hydrolytic enzymes (hydrolases) which typically comprise a catalytic domain containing the active site for substrate hydrolysis and a carbohydrate-binding domain for binding to the carbohydrate substrate in question. Such enzymes can comprise more than one catalytic domain and one, two or three carbohydrate-binding domains, and they may further comprise one or more polypeptide amino acid sequence regions linking the carbohydrate-binding domain(s) with the catalytic domain(s), a region of the latter type usually being denoted a "linker".

Examples of hydrolytic enzymes comprising a cellulose-binding domain are cellulases, xylanases, mannanases, arabinofuranosidases, acetylesterases and chitinases. "Cellulose-binding domains" have also been found in algae, e.g. in the red alga *Porphyra purpurea* in the form of a non-hydrolytic polysaccharide-binding protein [see P. Tomme et al., *Cellulose-Binding Domains—Classification* and *Properties*, in: *Enzymatic Degradation of Insoluble Carbohydrates*, John N. Saddler and Michael H. Penner (Eds.), ACS Symposium Series, No. 618 (1996)]. However, most of the known CBDs [which are classified and referred to by P. Tomme et al. (op cit.) as "cellulose-binding domains"] derive from cellulases and xylanases.

In the present context, the term "cellulose-binding domain" is intended to be understood in the same manner as in the latter reference (P. Tomme et al., op. cit). The P. Tomme et al. reference classifies more than 120 "cellulose-binding domains" into 10 families (I–X) which may have different functions or roles in connection with the mechanism of substrate binding. However, it is to be anticipated that new family representatives and additional families will appear in the future, and in connection with the present invention a representative of one such new CBD family has in fact been identified (see Example 2 herein).

In proteins/polypeptides in which CBDs occur (e.g. enzymes, typically hydrolytic enzymes such as cellulases), a CBD may be located at the N or C terminus or at an internal position.

That part of a polypeptide or protein (e.g. hydrolytic enzyme) which constitutes a CBD per se typically consists of more than about 30 and less than about 250 amino acid residues. For example: those CBDs listed and classified in Family I in accordance with P. Tomme et al. (op. cit.) consist of 33–37 amino acid residues, those listed and classified in Family IIa consist of 95–108 amino acid residues, those listed and classified in Family VI consist of 85–92 amino acid residues, whilst one CBD (derived from a cellulase from *Clostridium thermocellum*) listed and classified in Family VII consists of 240 amino acid residues. Accordingly, the molecular weight of an amino acid sequence constituting a CBD per se will typically be in the range of from about 4 kD to about 40 kD, and usually below about 35 kD.

Enzyme Hybrids

Enzyme classification numbers (EC numbers) referred to in the present specification with claims are in accordance with the *Recommendations* (1992) *of the Nomenclature Committee of the International Union of Biochemistry and Molecular Biology*, Academic Press Inc., 1992.

A modified enzyme (enzyme hybrid) for use in accordance with the invention comprises a catalytically active (enzymatically active) amino acid sequence (in general a polypeptide amino acid sequence) of an enzyme, more particularly of a non-cellulolytic enzyme (i.e. a catalytically active amino acid sequence of an enzyme other than a cellulase), useful in relation to desizing, in particular of an enzyme selected from the group consisting of amylases (e.g. α-amylases, EC 3.2.1.1) and lipases (e.g. triacylglycerol lipases, EC 3.1.1.3), fused (linked) to an amino acid sequence comprising a cellulose-binding domain. The catalytically active amino acid sequence in question may comprise or consist of, for example, the whole of—or substantially the whole of—the full amino acid sequence of the mature enzyme in question, or it may consist of a portion of the full sequence which retains substantially the same catalytic (enzymatic) properties as the full sequence.

Modified enzymes (enzyme hybrids) of the type in question, as well as detailed descriptions of the preparation and purification thereof, are known in the art [see, e.g., WO 90/00609, WO 94/24158 and WO 95/16782, as well as Greenwood et al., *Biotechnology and Bioengineering* 44 (1994) pp. 1295–1305]. They may, e.g., be prepared by transforming into a host cell a DNA construct comprising at least a fragment of DNA encoding the cellulose-binding domain ligated, with or without a linker, to a DNA sequence encoding the enzyme of interest, and growing the transformed host cell to express the fused gene. One relevant, but non-limiting, type of recombinant product (enzyme hybrid) obtainable in this manner—often referred to in the art as a "fusion protein"—may be described by one of the following general formulae:

A-CBD-MR-X-B

A-X-MR-CBD-B

In the latter formulae, CBD is an amino acid sequence comprising at least the cellulose-binding domain (CBD) per se.

MR (the middle region; a linker) may be a bond, or a linking group comprising from 1 to about 100 amino acid residues, in particular of from 2 to 40 amino acid residues, e.g. from 2 to 15 amino acid residues. MR may, in principle, alternatively be a non-amino-acid linker.

X is an amino acid sequence comprising the above-mentioned, catalytically (enzymatically) active sequence of amino acid residues of a polypeptide encoded by a DNA sequence encoding the non-cellulolytic enzyme of interest.

The moieties A and B are independently optional. When present, a moiety A or B constitutes a terminal extension of a CBD or X moiety, and normally comprises one or more amino acid residues.

It will thus, inter alia, be apparent from the above that a CBD in an enzyme hybrid of the type in question may be positioned C-terminally, N-terminally or internally in the enzyme hybrid. Correspondingly, an X moiety in an enzyme hybrid of the type in question may be positioned N-terminally, C-terminally or internally in the enzyme hybrid.

Enzyme hybrids of interest in the context of the invention include enzyme hybrids which comprise more than one CBD, e.g. such that two or more CBDs are linked directly to each other, or are separated from one another by means of spacer or linker sequences (consisting typically of a sequence of amino acid residues of appropriate length). Two CBDs in an enzyme hybrid of the type in question may, for example, also be separated from one another by means of an -MR-X- moiety as defined above.

A very important issue in the construction of enzyme hybrids of the type in question is the stability towards proteolytic degradation. Two- and multi-domain proteins are particularly susceptible towards proteolytic cleavage of linker regions connecting the domains. Proteases causing such cleavage may, for example, be subtilisins, which are known to often exhibit broad substrate specificities [see, e.g.: Grøn et al., *Biochemistry* 31 (1992), pp. 6011–6018; Teplyakov et al., *Protein Engineering* 5 (1992), pp. 413–420].

Glycosylation of linker residues in eukaryotes is one of Nature's ways of preventing proteolytic degradation. Another is to employ amino acids which are less favoured by the surrounding proteases. The length of the linker also plays a role in relation to accessibility by proteases. Which "solution" is optimal depends on the environment in which the enzyme hybrid is to function.

When constructing new enzyme hybrid molecules, linker stability thus becomes an issue of great importance. The various linkers described in examples presented herein (vide infra) in the context of the present invention are intended to take account of this issue.

Cellulases (Cellulase Genes) Useful for Preparation of CBDs

Techniques suitable for isolating a cellulase gene are well known in the art. In the present context, the terms "cellulase" and "cellulolytic enzyme" refer to an enzyme which catalyses the degradation of cellulose to glucose, cellobiose, triose and/or other cello-oligosaccharides.

Preferred cellulases (i.e. cellulases comprising preferred CBDs) in the present context are microbial cellulases, particularly bacterial or fungal cellulases. Endoglucanases, notably endo-1,4-β-glucanases (EC 3.2.1.4), particularly monocomponent (recombinant) endo-1,4-β-glucanases, are a preferred class of cellulases,.

Useful examples of bacterial cellulases are cellulases derived from or producible by bacteria from the group consisting of Pseudomonas, Bacillus, Cellulomonas, Clostridium, Microspora, Thermotoga, Caldocellum and Actinomycets such as Streptomyces, Termomonospora and Acidothemus, in particular from the group consisting of *Pseudomonas cellulolyticus, Bacillus lautus, Cellulomonas fimi, Clostridium thermocellum, Microspora bispora, Termomonospora fusca, Termomonospora cellulolyticum* and *Acidothemus cellulolyticus.*

The cellulase may be an acid, a neutral or an alkaline cellulase, i.e. exhibiting maximum cellulolytic activity in the acid, neutral or alkaline range, respectively.

A useful cellulase is an acid cellulase, preferably a fungal acid cellulase, which is derived from or producible by fungi from the group of genera consisting of Trichoderma, Myrothecium, Aspergillus, Phanaerochaete, Neurospora, Neocallimastix and Botrytis.

A preferred useful acid cellulase is one derived from or producible by fungi from the group of species consisting of *Trichoderma viride, Trichoderma reesei, Trichoderma longibrachiatum, Myrothecium verrucaria, Aspergillus niger, Aspergillus oryzae, Phanaerochaete chrysosporium, Neurospora crassa, Neocallimastix partriciarum* and *Botrytis cinerea.*

Another useful cellulase is a neutral or alkaline cellulase, preferably a fungal neutral or alkaline cellulase, which is derived from or producible by fungi from the group of genera consisting of Aspergillus, Penicillium, Myceliophthora, Humicola, Irpex, Fusarium, Stachybotrys, Scopulariopsis, Chaetomium, Mycogone, Verticillium, Myrothecium, Papulospora, Gliocladium, Cephalosporium and Acremonium.

A preferred alkaline cellulase is one derived from or producible by fungi from the group of species consisting of *Humicola insolens, Fusarium oxysporum, Myceliopthora thermophila, Penicillium janthinellum* and Cephalosporium sp., preferably from the group of species consisting of *Humicola insolens* DSM 1800, *Fusarium oxysporum* DSM 2672, *Myceliopthora thermophila* CBS 117.65, and Cephalosporium sp. RYM-202.

A preferred cellulase is an alkaline endoglucanase which is immunologically reactive with an antibody raised against a highly purified _43 kD endoglucanase derived from *Humicola insolens* DSM 1800, or which is a derivative of the latter _43 kD endoglucanase and exhibits cellulase activity.

Other examples of useful cellulases are variants of parent cellulases of fungal or bacterial origin, e.g. variants of a parent cellulase derivable from a strain of a species within the fungal genera Humicola, Trichoderma, Fusarium or Myceliophthora.

Isolation of a Cellulose-binding Domain

In order to isolate a cellulose-binding domain of, e.g., a cellulase, several genetic engineering approaches may be used. One method uses restriction enzymes to remove a portion of the gene and then to fuse the remaining gene-vector fragment in frame to obtain a mutated gene that encodes a protein truncated for a particular gene fragment. Another method involves the use of exonucleases such as Ba131 to systematically delete nucleotides either externally from the 5' and the 3' ends of the DNA or internally from a restricted gap within the gene. These gene-deletion methods result in a mutated gene encoding a shortened gene molecule whose expression product may then be evaluated for substrate-binding (e.g. cellulose-binding) ability. Appropriate substrates for evaluating the binding ability include cellulosic materials such as Avicel™ and cotton fibres. Other methods include the use of a selective or specific protease capable of cleaving a CBD, e.g. a terminal CBD, from the remainder of the polypeptide chain of the protein in question.

As already indicated (vide supra), once a nucleotide sequence encoding the substrate-binding (carbohydrate-binding) region has been identified, either as cDNA or chromosomal DNA, it may then be manipulated in a variety of ways to fuse it to a DNA sequence encoding the enzyme or enzymatically active amino acid sequence of interest. The DNA fragment encoding the carbohydrate-binding amino acid sequence, and the DNA encoding the enzyme or enzymatically active amino acid sequence of interest are then ligated with or without a linker. The resulting ligated DNA may then be manipulated in a variety of ways to achieve expression. Preferred microbial expression hosts include certain Aspergillus species (e.g. *A. niger* or *A. oryzae*), Bacillus species, and organisms such as *Escherichia coli* or *Saccharomyces cerevisiae.*

Amylolytic Enzymes

Amylases (e.g. α- or β-amylases) which are appropriate as the basis for enzyme hybrids of the types employed in the context of the present invention include those of bacterial or fungal origin. Chemically or genetically modified mutants of such amylases are included in this connection. Relevant α-amylases include, for example, α-amylases obtainable from Bacillus species, in particular a special strain of *B. licheniformis,* described in more detail in GB 1296839. Relevant commercially available amylases include Duramyl™, Termamyl™, Fungamyl™ and BAN™ (all available from Novo Nordisk A/S, Bagsvaerd, Denmark), and Rapidase™ and Maxamyl™ P (available from Gist-Brocades, Holland).

Other useful amylolytic enzymes are CGTases (cyclodextrin glucanotransferases, EC 2.4.1.19), e.g. those obtainable from species of Bacillus, Thermoanaerobactor or Thermoanaero-bacterium.

Lipolytic Enzymes

Lipolytic enzymes (lipases) which are appropriate as the basis for enzyme hybrids of the types employed in the context of the present invention include those of bacterial or fungal origin. Chemically or genetically modified mutants of such lipases are included in this connection.

Examples of useful lipases include a *Humicola lanuginosa* lipase, e.g. as described in EP 258 068 and EP 305 216; a *Rhizomucor miehei* lipase, e.g. as described in EP 238 023; a Candida lipase, such as a *C. antarctica* lipase, e.g. the *C. antarctica* lipase A or B described in EP 214 761; a Pseudomonas lipase, such as one of those described in EP 721 981 (e.g. a lipase obtainable from a Pseudomonas sp. SD705 strain having deposit accession number FERM BP-4772), in PCT/JP96/00426, in PCT/JP96/00454 (e.g. a *P. solanacearum* lipase), in EP 571 982 or in WO 95/14783 (e.g. a *P. mendocina* lipase), a *P. alcaligenes* or *P. pseudoalcaligenes* lipase, e.g. as described in EP 218 272, a *P.*

*cepacia* lipase, e.g. as described in EP 331 376, a *P. stutzeri* lipase, e.g. as disclosed in GB 1,372,034, or a *P. fluorescens* lipase; a Bacillus lipase, e.g. a *B. subtilis* lipase [Dartois et al., *Biochemica et Biophysica Acta* 1131 (1993) pp. 253–260], a *B. stearothennophilus* lipase (JP 64/744992) and a *B. pumilus* lipase (WO 91/16422).

Furthermore, a number of cloned lipases may be useful, including the *Penicillium camembertii* lipase described by Yamaguchi et al. in *Gene* 103 (1991), pp. 61–67, the *Geotricum candidum* lipase [Y. Schimada et al., *J. Biochem.* 106 (1989), pp. 383–388], and various Rhizopus lipases such as an *R. delemar* lipase [M. J. Hass et al., *Gene* 109 (1991) pp. 117–113], an *R. niveus* lipase [Kugimiya et al., *Biosci. Biotech. Biochem.* 56 (1992), pp. 716–719] and a *R. oryzae* lipase.

Other potentially useful types of lipolytic enzymes include cutinases, e.g. a cutinase derived from *Pseudomonas mendocina* as described in WO 88/09367, or a cutinase derived from *Fusarium solani* f. pisi (described, e.g., in WO 90/09446).

Suitable commercially available lipases include Lipolase™ and Lipolase Ultra™ (available from Novo Nordisk A/S), M1 Lipase™, Lumafast™ and Lipomax™ (available from Gist-Brocades) and Lipase P "Amano" (available from Amano Pharmaceutical Co. Ltd.).

Plasmids

Preparation of plasmids capable of expressing fusion proteins having the amino acid sequences derived from fragments of more than one polypeptide is well known in the art (see, for example, WO 90/00609 and WO 95/16782). The expression cassette may be included within a replication system for episomal maintenance in an appropriate cellular host or may be provided without a replication system, where it may become integrated into the host genome. The DNA may be introduced into the host in accordance with known techniques such as transformation, microinjection or the like.

Once the fused gene has been introduced into the appropriate host, the host may be grown to express the fused gene. Normally it is desirable additionally to add a signal sequence which provides for secretion of the fused gene. Typical examples of useful fused genes are:

Signal sequence—(pro-peptide)—carbohydrate-binding domain—linker—enzyme sequence of interest, or Signal sequence—(pro-peptide)—enzyme sequence of interest—linker—carbohydrate-binding domain, in which the pro-peptide sequence normally contains 5–100, e.g. 5–25, amino acid residues.

The recombinant product may be glycosylated or non-glycosylated.

Determination of α-amylolytic Activity (KNU)

The α-amylolytic activity of an enzyme or enzyme hybrid may be determined using potato starch as substrate. This method is based on the break-down (hydrolysis) of modified potato starch, and the reaction is followed by mixing samples of the starch/enzyme or starch/enzyme hybrid solution with an iodine solution. Initially, a blackish-blue colour is formed, but during the break-down of the starch the blue colour becomes weaker and gradually turns to a reddish-brown. The resulting colour is compared with coloured glass calibration standards.

One Kilo Novo α-Amylase Unit (KNU) is defined as the amount of enzyme (enzyme hybrid) which, under standard conditions (i.e. at 37±0.05° C., 0.0003 M $Ca^{2+}$, pH 5.6) dextrinizes 5.26 g starch dry substance (Merck Amylum solubile) per hour.

Determination of Lipolytic Activity (LU)

The lipolytic (lipase) activity of an enzyme or enzyme hybrid may be determined using tributyrin (glyceryl tributyrate) as substrate. This method is based on the hydrolysis of tributyrin by the enzyme or enzyme hybrid, and the alkali consumption is registered as a function of time.

One Lipase Unit (LU) is defined as the amount of enzyme (enzyme hybrid) which, under standard conditions (i.e. at 30.0° C., pH 7.0; with Gum Arabic as emulsifier and tributyrin as substrate) liberates 1 $\mu$mol of titratable butyric acid per minute.

Process Conditions

It will be understood that the method of the invention may be performed in accordance with any suitable desizing procedure known in the art, e.g. as described by E. S. Olson in *Textile Wet Processes, Vol. I*, Noyes Publication, Park Ridge, N.J., USA (1983), or by M. Peter and H. K. Rouette in *Grundlagen der Textilveredlung*, Deutsche Fachverlag GmbH, Frankfurt am Main, Germany (1988). Thus, the process conditions to be used in performing the present invention may be selected so as to match particular equipment or a particular type of process which it is desirable to use. Preferred examples of types of procedures suitable for use in connection with the present invention include Jigger/Winch, Pad-Roll and Pad-Steam types. These types are dealt with in further detail below.

The process of the invention may be carried out as a batch, semi-continuous or continuous process. As an example, the process may comprise the following steps:

(a) impregnating the fabric in a desizing bath containing (as a minimum) an amylolytic enzyme hybrid and/or a lipolytic enzyme hybrid;

(b) subjecting the impregnated fabric to steaming, so as to bring the fabric to the desired reaction temperature, generally between 20° and 120° C.; and (c) holding by rolling-up or pleating the cloth in a J-Box, U-Box, carpet machine or the like for a sufficient period of time (normally between a few minutes and several hours) to allow the desizing to occur.

Prior to carrying out the chosen treatment, the amylolytic enzyme hybrid and/or the lipolytic enzyme hybrid may conveniently be mixed with other components which are conventionally used in the desizing process.

Further components required for performance of the process may be added separately. Thus, for example, a wetting agent and, optionally, a stabilizer may be added. The stabilizer in question may be an agent stabilizing the amylolytic enzyme hybrid and/or the lipolytic enzyme hybrid. Wetting agents serve to improve the wettability of the fibre, whereby rapid and even desizing may be achieved. The wetting agent is preferably of an oxidation-stable type.

In a preferred embodiment of the process of the invention, an amylolytic enzyme hybrid is used in an amount corresponding to an amylase activity in the range of between 1 and 5000 KNU per liter of desizing liquor, such as between 10 and 1000 KNU per liter of desizing liquor, preferably between 50 and 500 KNU per liter, more preferably between 20 and 500 KNU per liter of desizing liquor.

In a preferred embodiment of the process of the invention, a lipolytic enzyme hybrid is used in an amount corresponding to a lipase activity in the range of between 10 and 20000 LU per liter of desizing liquor, such as between 50 and 10000 LU per liter of desizing liquor, more preferably between 100 and 5000 LU per liter of desizing liquor.

Irrespective of the particular type of procedure to be used for the desizing, the process of the invention is normally performed at a temperature in the range of 30–100° C., such as 35–60° C., and at a pH in the range of 3–11, preferably 7–9. However, the actual process conditions may vary widely within these ranges.

It will be understood that the process may be performed in any equipment sufficiently tolerant towards the process conditions in question.

The process of the invention may be employed alone or in combination with one or more other enzymatic desizing processes. Suitable combinations include the following:

a treatment with an amylolytic enzyme hybrid, and a treatment with a cellulase;

a treatment with a lipolytic enzyme hybrid, and a treatment with a cellulase;

a treatment with an amylolytic enzyme hybrid, and a treatment with a lipase or a lipolytic enzyme hybrid;

a treatment with a lipolytic enzyme hybrid, and a treatment with an amylase or an amylolytic enzyme hybrid;

a treatment with an amylolytic enzyme hybrid, and a treatment with a lipase or a lipolytic enzyme hybrid, and a treatment with a cellulase;

a treatment with a lipolytic enzyme hybrid, and a treatment with an amylase or an amylolytic enzyme hybrid, and a treatment with a cellulase.

The various enzymes/enzyme hybrids will normally be added in one step, but the desizing process may also be performed in more than one step, taking one enzyme/enzyme hybrid at a time.

Composition of the Invention

Although an enzyme hybrid, e.g. amylolytic enzyme hybrid and/or lipolytic enzyme hybrid, may be added as such, it is preferred that it is formulated in the form of a suitable desizing composition.

The desizing composition of the invention may comprise a single type of enzyme hybrid, or more than one type of enzyme hybrid (e.g. an amylolytic enzyme hybrid together with a lipolytic enzyme hybrid). The composition may be in the form of, e.g., a granulate, preferably a non-dusting granulate, or a liquid, in particular a stabilized liquid, or a slurry, or in a protected form. Non-dusting granulates may be produced, for example, as disclosed in U.S. Pat. No. 4,106,991 and U.S. Pat. No. 4,661,452 (both to Novo Nordisk A/S) and may optionally be coated by methods known in the art. In the case of granular formulations ("granulates"), different enzyme hybrids may be formulated, for example, either as a single granulate wherein the individual granules each contain all the enzyme hybrids in question, or as a mixture of discrete, different granulates wherein the individual granules each contain one type of enzyme hybrid of the kind in question.

Liquid enzyme preparations may, for instance, be stabilized by adding a polyol (such as propylene glycol or another glycol), a sugar, a sugar alcohol or acetic acid, according to established procedures. Other enzyme stabilizers are well known in the art. Protected enzymes may be prepared as disclosed in EP 238 216.

The composition of the invention may comprise a wetting agent and/or, optionally, one or more further components selected from the group consisting of dispersing agents, sequestering agents (and/or precipitants) and emulsifying agents. An example of a suitable wetting agent is the commercial product Arbyl™ R, available from Grünau, Germany. An emulsifying agent serves to emulsify hydrophobic impurities which may be present on the fabric. A dispersing agent serves to prevent the redeposition of extracted impurities on the fabric. A sequestering agent or precipitant serves to remove metal ions (such as $Ca^{2+}$, $Mg^{2+}$ and $Fe^{2+}$) which may have a negative impact on the process; suitable examples include caustic soda (sodium hydroxide) and soda ash (sodium carbonate).

A further aspect of the invention relates to a DNA construct disclosed herein which encodes, or which comprises a sequence which encodes, an enzyme hybrid as disclosed in the present specification.

A still further aspect of the invention relates to a polypeptide (fusion protein or enzyme hybrid) which is encoded by such a DNA construct or sequence, and/or which is disclosed in the present specification.

The invention is further illustrated by means of the examples given below, which are in no way intended to limit the scope of the invention as claimed:

MATERIALS AND METHODS

Strains:

*Bacillus agaradherens* NCIMB No. 40482: comprises the endoglucanase enzyme encoding DNA sequence of Example 2, below.

*Escherichia coli* SJ2 [Diderichsen et al., *J. Bacteriol.* 172 (1990), pp. 4315–4321].

Electrocompetent cells prepared and transformed using a Bio-Rad GenePulser™ as recommended by the manufacturer.

*Bacillus subtilis* PL2306: this strain is the *B. subtilis* DN1885 with disrupted apr and npr genes [Diderichsen et al., *J. Bacteriol.* 172 (1990), pp. 4315–4321] disrupted in the transcriptional unit of the known *Bacillus subtilis* cellulase gene, resulting in cellulase-negative cells. The disruption was performed essentially as described in Sonenshein et al. (Eds.), *Bacillus subtilis and other Gram-Positive Bacteria*, American Society for Microbiology (1993), p.618.

Plasmids:

pDN1528 [Jørgensen et al., *J. Bacteriol.* 173 (1991), p.559–567].

pBluescriptKSII- (Stratagene, USA).

pDN1981 [Jørgensen et al., *Gene* 96 (1990), p. 37–41].

Solutions/Media

TY and LB agar [as described in Ausubel et al. (Eds.), *Current Protocols in Molecular Biology*, John Wiley and Sons (1995)].

SB: 32 g Tryptone, 20 g yeast extract, 5 g sodium chloride and 5 ml 1 N sodium hydroxide are mixed in sterile water to a final volume of 1 liter. The solution is sterilised by autoclaving for 20 minutes at 121 ° C.

10% Avicel™: 100 g of Avicel™ (FLUKA, Switzerland) is mixed with sterile water to a final volume of 1 liter, and the resulting 10% Avicel™ is sterilised by autoclaving for 20 minutes at 121° C.

Buffer: 0.05 M potassium phosphate, pH 7.5.

General Molecular Biology Methods

DNA manipulations and transformations were performed using standard methods of molecular biology [Sambrook et al., *Molecular Cloning: A Laboratory Manual*, Cold Spring Harbor lab., Cold Spring Harbor, N.Y. (1989); Ausubel et al. (Eds.), *Current Protocols in Molecular Biology*, John Wiley and Sons (1995); C. R. Harwood and S. M. Cutting (Eds.) *Molecular Biological Methods for Bacillus*, John Wiley and Sons (1990)].

Enzymes for DNA manipulations were used according to the specifications of the suppliers.

EXAMPLE 1

Subcloning of a Partial Termamyl Sequence.

The alpha-amylase gene encoded on pDN1528 was PCR amplified for introduction of a BamHI site in the 3'-end of the coding region. The PCR and the cloning were carried out as follows:

Approximately 10–20 ng of plasmid pDN1528 was PCR amplified in HiFidelity™ PCR buffer (Boehringer Mannheim, Germany) supplemented with 200 µM of each dNTP, 2.6 units of HiFidelity™ Expand enzyme mix, and 300 pmol of each primer:
5289

5'-GCT TTA CGC CCG ATT GCT GAC GCT G -3' (SEQ ID No. 12)
26748

5'-GCG ATG AGA CGC GCG GCC GCC TAT CTT TGA ACA TAA ATT GAA AC<u>G GAT CC</u>G -3' (SEQ ID No. 13)
(BamHI restriction site underlined).

The PCR reactions were performed using a DNA thermal cycler (Landgraf, Germany). One incubation at 94° C. for 2 min, 60° C. for 30 sec and 72° C. for 45 sec was followed by ten cycles of PCR performed using a cycle profile of denaturation at 94° C. for 30 sec, annealing at 60° C. for 30 sec, and extension at 72° C. for 45 sec and twenty cycles of denaturation at 94° C. for 30 sec, 60° C. for 30 sec and 72° C. for 45 sec (at this elongation step, 20 sec are added every cycle). 10 µl aliquots of amplification product were analyzed by electrophoresis in 1.0% agarose gels (NuSieve™, FMC) with ReadyLoad™ 100 bp DNA ladder (GibcoBRL, Denmark) as a size marker.

40 µl aliquots of PCR product generated as described above were purified using QIAquick™ PCR purification kit (Qiagen, USA) according to the manufacturer's instructions. The purified DNA was eluted in 50 µl of 10 mM Tris-HCl, pH 8.5. 25 µl of the purified PCR fragment was digested with BamHI and PstI, subjected to electrophoresis in 1.0% low gelling temperature agarose (SeaPlaque™ GTG, FMC) gels, and the relevant fragment was excised from the gel and purified using QIAquick™ Gel extraction Kit (Qiagen, USA) according to the manufacturer's instructions. The isolated DNA fragment was then ligated to BamHI-PstI digested pBluescriptII KS-, and the ligation mixture was used to transform *E. coli* SJ2.

Cells were plated on LB agar plates containing Ampicillin (200 µg/ml) and supplemented with X-gal (5-bromo-4-chloro-3-indolyl-α-D-galactopyranoside, 50 µg/ml), and incubated at 37° C. overnight. The next day, white colonies were restreaked onto fresh LB-Ampicillin agar plates and incubated at 37° C. overnight. The following day, single colonies were transferred to liquid LB medium containing Ampicillin (200 µg/ml) and incubated overnight at 37° C. with shaking at 250 rpm.

Plasmids were extracted from the liquid cultures using QIAgen Plasmid Purification mini kit (Qiagen, USA) according to the manufacturer's instructions. 5 µl samples of the plasmids were digested with PstI and BamHI. The digestions were checked by gel electrophoresis on a 1.0% agarose gel (NuSieve™, FMC). One positive clone, containing the PstI-BamHI fragment containing part of the α-amylase gene, was designated pMB335. This plasmid was then used in the construction of α-amylase-CBD hybrid.

Isolation of Genomic DNA

*Clostridium stercorarium* NCIMB 11754 was grown anaerobically at 60° C. in specified media as recommended by The National Collections of Industrial and Marine Bacteria Ltd. (NCIMB), Scotland. Cells were harvested by centrifugation.

Genomic DNA was isolated as described by Pitcher et al, *Lett. Appl. Microbiol.* 8 (1989), pp. 151–156.

In Vitro Amplification of the CBD-dimer of *Clostridium stercorarium* (NCIMB 11754) XynA Approximately 100–200 ng of genomic DNA was PCR amplified in HiFidelity™ PCR buffer (Boehringer Mannheim, Germany) supplemented with 200 µM of each dNTP, 2.6 units of HiFidelity™ Expand enzyme mix, and 300 pmol of each primer:
27183

```
                                           (SEQ ID No. 14)
5'-GCT GCA GGA TCC GTT TCA ATT TAT GTT CAA AGA

TCT GGC GGA CCT GGA ACG CCA AAT AAT GGA AGA GG -3'
```

27182

5'-GCA CTA GCT AGA <u>CGG CCG</u> CTA CCA GTC AAC ATT AAC AGG ACC TGA G-3' (SEQ ID No. 15)
(BamHI and EagI restriction sites underlined).

The primers were designed to amplify the DNA encoding the cellulose-binding domain of the XynA-encoding gene of *Clostridium stercorarium* NCIMB 11754; the DNA sequence was extracted from the database GenBank under the accession number D13325.

The PCR reactions were performed using a DNA thermal cycler (Landgraf, Germany). One incubation at 94° C. for 2 min, 60° C. for 30 sec and 72° C. for 45 sec was followed by ten cycles of PCR performed using a cycle profile of denaturation at 94° C. for 30 sec, annealing at 60° C. for 30 sec, and extension at 72° C. for 45 sec and twenty cycles of denaturation at 94° C. for 30 sec, 60° C. for 30 sec and 72° C. for 45 sec (at this elongation step, 20 sec are added every cycle). 10 µl aliquots of amplification product were analyzed by electrophoresis in 1.0% agarose gels (NuSieve™, FMC) with ReadyLoad™ 100 bp DNA ladder (GibcoBRL, Denmark) as a size marker.

Cloning by Polymerase Chain Reaction (PCR):
Subcloning of PCR Fragments.

40 µl aliquots of PCR product generated as described above were purified using QIAquick™ PCR purification kit (Qiagen, USA) according to the manufacturer's instructions. The purified DNA was eluted in 50 µl of 10 mM Tris-HCl, pH 8.5. 25 µl of the purified PCR fragment was digested with BamHI and EagI, subjected to electrophoresis in 1.0% low gelling temperature agarose (SeaPlaque™ GTG, FMC) gels, and the relevant fragment was excised from the gels and purified using QIAquick™ Gel extraction Kit (Qiagen, USA) according to the manufacturer's instructions. The isolated DNA fragment was then ligated to BamHI-NotI digested pMB335 and the ligation mixture was used to transform *E. coli* SJ2.

Identification and Characterization of Positive Clones

Cells were plated on LB agar plates containing Ampicillin (200 µg/ml) and incubated at 37° C. overnight. The next day, colonies were restreaked onto fresh LB-Ampicillin agar plates and incubated at 37° C. overnight. The following day, single colonies were transferred to liquid LB medium containing Ampicillin (200 µg/ml) and incubated overnight at 37° C. with shaking at 250 rpm.

Plasmids were extracted from the liquid cultures using QIAgen Plasmid Purification mini kit (Qiagen, USA) according to the manufacturer's instructions. 5 µl samples of the plasmids were digested with BamHI and NotII. The digestions were checked by gel electrophoresis on a 1.0% agarose gel (NuSieve™, FMC). The appearance of a DNA fragment of the same size as seen from the PCR amplification indicated a positive clone.

One positive clone, containing the fusion construct of the α-amylase gene and the CBD-dimer of *Clostridium stercorarium* (NCIMB 11754) XynA, was designated MBamyX.

Cloning of the Fusion Construct into a Bacillus-based Expression Vector

The pDN1528 vector contains the amyL gene of *B. licheniformis*; this gene is actively expressed in *B. subtilis*, resulting in the production of active α-amylase appearing in the supernatant. For expression purposes, the DNA encoding the fusion protein as constructed above was introduced to pDN1528.

This was done by digesting pMBamyX and pDN1528 with SalI-NotI, purifying the fragments and ligating the 4.7 kb pDN1528 SalI-NotI fragment with the 1.0 kb pMBamyX SalI-NotI fragment. This created an inframe fusion of the hybrid construction with the Termamyl™ (*B. licheniformis* α-amylase) gene. The DNA sequence of the fusion construction of pMB206, and the corresponding amino acid sequence, are shown in SEQ ID No. 1 and SEQ ID No. 2, respectively.

The ligation mixture was used to transform competent cells of *B. subtilis* PL2306. Cells were plated on LB agar plates containing chloramphenicol (6 μg/ml), 0.4% glucose and 10 mM potassium hydrogen phosphate, and incubated at 37° C. overnight. The next day, colonies were restreaked onto fresh LBPG (LB plates with 0.4% glucose and 10 mM potassium phosphate, pH 10) chloramphenicol agar plates and incubated at 37° C. overnight. The following day, single colonies of each clone were transferred to liquid LB medium containing chloramphenicol (6 μg/ml) and incubated overnight at 37° C. with shaking at 250 rpm.

Plasmids were extracted from the liquid cultures using QIAgen Plasmid Purification mini kit (Qiagen, USA) according to the manufacturer's instructions. However, the resuspension buffer was supplemented with 1 mg/ml of chicken egg white lysozyme (SIGMA, USA) prior to lysing the cells at 37° C. for 15 minutes. 5 μl samples of the plasmids were digested with BamHI and NotI. The digestions were checked by gel electrophoresis on a 1.5% agarose gel (NuSieve™, FMC). The appearance of a DNA fragment of the same size as seen from the PCR amplification indicated a positive clone. One positive clone was designated MB-BSamyx.

Expression, Secretion and Functional Analysis of the Fusion Protein

The clone MB-BSamyx (expressing Termamyl™ fused to *C. stercorarium* XynA dimer CBD) was incubated for 20 hours in SB medium at 37° C. with shaking at 250 rpm. 1 ml of cell-free supernatant was mixed with 200 μl of 10% Avicel™. The mixture was incubated for 1 hour at 0° C. and then centrifuged for 5 minutes at 5000×g. The pellet was resuspended in 100 μl of SDS-PAGE buffer, and the suspension was boiled at 95° C. for 5 minutes, centrifuged at 5000×g for 5 minutes, and 25 μl was loaded onto a 4–20% Laemmli Tris-Glycine, SDS-PAGE NOVEX™ gel (Novex, USA). The samples were subjected to electrophoresis in an Xcell™ Mini-Cell (NOVEX, USA) as recommended by the manufacturer. All subsequent handling of gels, including staining (Coomassie), destaining and drying, were performed as described by the manufacturer.

The appearance of a protein band of molecular weight approx. 85 kDa indicated expression in *B. subtilis* of the Termamyl-CBD fusion amyx.

EXAMPLE 2

Identification of a Novel CBD Representing a New CBD Family

The alkaline cellulase cloned in *Bacillus subtilis* as described below was expressed by incubating the clone for 20 hours in SB medium at 37° C. with shaking at 250 rpm. The expressed cellulase was shown to contain a CBD by its ability to specifically bind to Avicel™.

When left to incubate for a further 20 hours, the cellulase was proteolytically cleaved and two specific protein bands appeared in SDS-PAGE, one corresponding to the catalytic part of the cellulase, approximate molecular weight (MW) 35 kD, and the other corresponding to a proposed linker and CBD of approximate MW 8 kD.

The CBD was found to be the C-terminal part of the cellulase, and did not match any of the CBD families described previously [Tomme et al., *Cellulose-Binding Domains: Classification and Properties*, In: J. N. Saddler and M. H. Penner (Eds.), *Enzymatic Degradation of Insoluble Carbohydrates*, ACS Symposium Series No. 618 (1996)]. Accordingly, this CBD appears to be the first member of a new family.

Cloning of the Alkaline Cellulase (Endoglucanase) from *Bacillus agaradherens* and Expression of the Alkaline Cellulase in *Bacillus subtilis*

The nucleotide sequence encoding the alkaline cellulase from *Bacillus agaradherens* (deposited under accession No. NCIMB 40482) was cloned by PCR for introduction in an expression plasmid pDN1981. PCR was performed essentially as described above on 500 ng of genomic DNA, using the following two primers containing NdeI and KpnI restriction sites for introducing the endoglucanase-encoding DNA sequence to pDN1981 for expression:

20887

(SEQ ID No. 16)
5'-GTA GGC TCA GT<u>C ATA TGT</u> TAC ACA TTG AAA GGG GAG

GAG AAT CAT GAA AAA GAT AAC TAC TAT TTT TGT CG-3'

21318

5'-GTA CCT CGC <u>GGG TAC C</u>AA GCG GCC GCT TAA TTG AGT GGT TCC CAC GGA CCG-3' (SEQ ID No. 17)

After PCR cycling, the PCR fragment was purified using QIAquick™ PCR column kit (Qiagen, USA) according to the manufacturer's instructions. The purified DNA was eluted in 50 μl of 10 mM Tris-HCl, pH 8.5, digested with NdeI and KpnI, purified and ligated to digested pDN1981. The ligation mixture was used to transform *B. subtilis* PL2306. Competent cells were prepared and transformed as described by Yasbin et al., *J. Bacteriol.* 121 (1975), pp. 296–304.

Isolation and Testing of *B. subtilis* Transformants

The transformed cells were plated on LB agar plates containing Kanamycin (10 mg/ml), 0.4% glucose, 10 mM potassium phosphate and 0.1% AZCL HE-cellulose (Megazyme, Australia), and incubated at 37° C. for 18 hours. Endoglucanase-positive colonies were identified as colonies surrounded by a blue halo.

Each of the positive transformants was inoculated in 10 ml TY medium containing Kanamycin (10 mg/ml). After 1 day of incubation at 37° C. with shaking at 250 rpm, 50 ml of supernatant was removed. The endoglucanase activity was identified by adding 50 ml of supernatant to holes punctured in the agar of LB agar plates containing 0.1% AZCL HE-cellulose.

After 16 hours incubation at 37° C., blue halos surrounding holes indicated expression of the endoglucanase in *B. subtilis*. One such clone was designated MB208. The encoding DNA sequence and amino acid sequence of the endoglucanase are shown in SEQ ID No. 3 and SEQ ID No. 4, respectively.

The DNA sequence was determined as follows: Qiagen purified plasmid DNA was sequenced with the Taq deoxy terminal cycle sequencing kit (Perkin Elmer, USA) using the primers #21318 and #20887 (vide supra) and employing an Applied Biosystems 373A automated sequencer operated according to the manufacturer's instructions. Analysis of the sequence data is performed according to Devereux et al., *Carcinogenesis* 14 (1993), pp. 795–801.

In Vitro Amplification of the CBD of *Bacillus agaradherens* NCIMB 40482 Endoglucanase Approximately 10–20 ng of plasmid pMB208 was PCR amplified in HiFidelity™ PCR buffer (Boehringer Mannheim, Germany) supplemented with 200 μM of each dNTP, 2.6 units of HiFidelity™ Expand enzyme mix and 300 pmol of each primer:
27184

(SEQ ID No. 18)
5'-GCT GCA <u>GGA TCC</u> GTT TCA ATT TAT GTT CAA AGA TCT
CCT GGA GAG TAT CCA GCA TGG GAC CCA A-3'

28495
5'-GC ACA AGC <u>TTG CGG CCG CTA ATT GAG TGG TTC CCA CGG ACC G</u> -3' (SEQ ID No. 19)
(BamHI and NotI restriction sites underlined).

The primers were designed to amplify the CBD-encoding DNA of the cellulase-encoding gene of *Bacillus agaradherens* NCIMB 40482.

The PCR reaction was performed using a DNA thermal cycler (Landgraf, Germany). One incubation at 94° C. for 2 min, 60° C. for 30 sec and 72° C. for 45 sec was followed by ten cycles of PCR performed using a cycle profile of denaturation at 94° C. for 30 sec, annealing at 60° C. for 30 sec, and extension at 72° C. for 45 sec and twenty cycles of denaturation at 94° C. for 30 sec, 60° C. for 30 sec and 72° C. for 45 sec (at this elongation step, 20 sec are added every cycle). 10 μl aliquots of amplification product were analyzed by electrophoresis in 1.5% agarose gels (NuSieve™, FMC) with ReadyLoad™ 100 bp DNA ladder (GibcoBRL, Denmark) as a size marker.

Cloning by Polymerase Chain Reaction (PCR):
Subcloning of PCR Fragments

40 μl aliquots of PCR products generated as described above were purified using QIAquick™ PCR purification kit (Qiagen, USA) according to the manufacturer's instructions. The purified DNA was eluted in 50 μl of 10 mM Tris-HCl, pH 8.5. 25 μl of the purified PCR fragment was digested with BamHI and NotI, subjected to electrophoresis in 1.5% low gelling temperature agarose (SeaPlaque™ GTG, FMC) gels, and the relevant fragment was excised from the gels and purified using QIAquick™ Gel extraction kit (Qiagen, USA) according to the manufacturer's instructions. The isolated DNA fragment was then ligated to BamHI-NotI digested pMB335, and the ligation mixture was used to transform *E. coli* SJ2.

Identification and Characterization of Positive Clones

Cells were plated on LB agar plates containing Ampicillin (200 μg/ml) and incubated at 37° C. overnight. The next day, colonies were restreaked onto fresh LB-Ampicillin agar plates and incubated at 37° C. overnight. The following day, single colonies were transferred to liquid LB medium containing Ampicillin (200 μg/ml) and incubated overnight at 37° C. with shaking at 250 rpm.

Plasmids were extracted from the liquid cultures using QIAgen Plasmid Purification mini kit (Qiagen, USA) according to the manufacturer's instructions. 5 μl samples of the plasmids were digested with BamHI and NotI. The digestions were checked by gel electrophoresis on a 1.5% agarose gel (NuSieve™, FMC). The appearance of a DNA fragment of the same size as seen from the PCR amplification indicated a positive clone.

One positive clone, containing the fusion construct of the Termamyl™ (α-amylase gene and the CBD of *Bacillus agaradherens* NCIMB 40482 alkaline cellulase Cel5A, was designated MBamyC5A.

Cloning of the Fusion Construct into a Bacillus-based Expression Vector

As mentioned previously, the amyL gene of *B. licheniformis* (contained in the pDN1528 vector) is actively expressed in *B. subtilis*, resulting in the production of active α-amylase appearing in the supernatant. For expression purposes, the DNA encoding the fusion protein as constructed above was introduced to pDN1528. This was done by digesting pMBamyC5A and pDN1528 with SalI-NotI, purifying the fragments and ligating the 4.7 kb pDN1528 SalI-NotI fragment with the 0.5 kb pMBamyC5A SalI-NotI fragment. This created an inframe fusion of the hybrid construction with the Termamyl™ gene. The DNA sequence of the fusion construction of pMB378, and the corresponding amino acid sequence, are shown in SEQ ID No. 5 and SEQ ID No. 6, respectively.

The ligation mixture was used to transform competent cells of *B. subtilis* PL2306. Cells were plated on LB agar plates containing chloramphenicol (6 μg/ml), 0.4% glucose and 10 mM potassium hydrogen phosphate, and incubated at 37° C. overnight. The next day, colonies were restreaked onto fresh LBPG chloramphenicol agar plates and incubated at 37° C. overnight. The following day, single colonies of each clone were transferred to liquid LB medium containing chloramphenicol (6 μg/ml) and incubated overnight at 37° C. with shaking at 250 rpm.

Plasmids were extracted from the liquid cultures using QIAgen Plasmid Purification mini kit (Qiagen, USA) according to the manufacturer's instructions. However, the resuspension buffer was supplemented with 1 mg/ml of chicken egg white lysozyme (SIGMA, USA) prior to lysing the cells at 37° C. for 15 minutes. 5 μl samples of the plasmids were digested with BamHI and NotI. The digestions were checked by gel electrophoresis on a 1.5% agarose gel (NuSieve™, FMC). The appearance of a DNA fragment of the same size as seen from the PCR amplification indicated a positive clone. One positive clone was designated MB378.

Expression, Secretion and Functional Analysis of the Fusion Protein

The clone MB378 (expressing Termamyl™ fused to *Bacillus agaradherens* Cel5A CBD) was incubated for 20 hours in SB medium at 37° C. with shaking at 250 rpm. 1 ml of cell-free supernatant was mixed with 200 μl of 10% Avicel™. The mixture was incubated for 1 hour at 0° C. and then centrifuged for 5 minutes at 5000×g. The pellet was resuspended in 100 μl of SDS-PAGE buffer, and the suspension was boiled at 95° C. for 5 minutes, centrifuged at 5000×g for 5 minutes, and 25 μl was loaded onto a 4–20% Laemmli Tris-Glycine, SDS-PAGE NOVEX™ gel (Novex, USA). The samples were subjected to electrophoresis in an Xcell™ Mini-Cell (NOVEX, USA) as recommended by the manufacturer. All subsequent handling of gels, including staining (Coomassie), destaining and drying, were performed as described by the manufacturer.

The appearance of a protein band of molecular weight approx. 60 kDa indicated expression in *B. subtilis* of the Termamyl™-CBD fusion encoded on the plasmid pMB378.

EXAMPLE 3

This example describes fusion of Termamyl™ and the CBD from *Cellulomonas fimi* (ATCC 484) cenA gene using the sequence overlap extension (SOE) procedure [see, e.g., Sambrook et al., Ausubel et al., or C. R. Harwood and S. M. Cutting (loc. cit.)]. The final construction is as follows:

Termamyl™ promoter—Termamyl™ signal peptide—cenA CBD—linker—mature Termamyl™.

Amplification of the Termamyl™ Fragment for SOE

Approximately 10–20 ng of plasmid pDN1528 was PCR amplified in HiFidelity™ PCR buffer (Boehringer Mannheim, Germany) supplemented with 200 μM of each dNTP, 2.6 units of HiFidelity™ Expand enzyme mix, and 100 pmol of each primer:
4576

5'-CTC GTC CCA ATC GGT TCC GTC -3' (SEQ ID No. 20)

28403

(SEQ ID No. 21)
5'-TGC ACT GGT ACA GTT CCT ACA ACT AGT CCT ACA CGT GCA AAT CTT AAT GGG ACG CTG-3'

The part of the primer #28403 constituting a fragment of the Termamyl™ sequence is underlined. The sequence on the 5' side of this underlined sequence is that coding for the linker region to the CBD.

The PCR reaction was performed using a DNA thermal cycler (Landgraf, Germany). One incubation at 94° C. for 2 min, 55° C. for 30 sec and 72° C. for 45 sec was followed by twenty cycles of PCR performed using a cycle profile of denaturation at 96° C. for 10 sec, annealing at 55° C. for 30 sec, and extension at 72° C. for 45 sec. 10 μl aliquots of the amplification product were analyzed by electrophoresis in 1.0% agarose gels (NuSieve™, FMC) with ReadyLoad™ 100 bp DNA ladder (GibcoBRL, Denmark) as a size marker.

40 μl aliquots of the PCR product generated as described above were purified using QIAquick™ PCR purification kit (Qiagen, USA) according to the manufacturer's instructions. The purified DNA was eluted in 50 μl of 10 mM Tris-HCl, pH 8.5.

Isolation of Genomic DNA

*Cellulomonas fimi* ATCC 484 was grown in TY medium at 30° C. with shaking at 250 rpm for 24 hours. Cells were harvested by centrifugation.

Genomic DNA was isolated as described by Pitcher et al., *Lett. Appl. Microbiol.* 8 (1989), pp. 151–156.

In Vitro Amplification of the CBD of *Cellulomonas fimi* (ATCC 484) cenA Gene for SOE Procedure Approximately 100–200 ng of genomic DNA was PCR amplified in HiFidelity™ PCR buffer (Boehringer Mannheim, Germany) supplemented with 200 μM of each dNTP, 2.6 units of HiFidelity™ Expand enzyme mix, and 100 pmol of each primer:
8828

(SEQ ID No. 22)
5'-CTG CCT CAT TCT GCA GCA GCG GCG GCA AAT CTT AAT GCT CCC GGC TGC CGC GTC GAC TAC -3'

28404

5'-TGT AGG AAC TGT ACC AGT GCA CGT GGT GCC GTT GAG C -3' (SEQ ID No. 23)

(Pst restriction site underlined).

The primers were designed to amplify the DNA encoding the cellulose-binding domain of the CenA-encoding gene of *Cellulomonas fimi* (ATCC 484). The DNA sequence was extracted from the database GenBank under the accession number M15823.

PCR cycling was performed as follows: One incubation at 94° C. for 2 min, 55° C. for 30 sec and 72° C. for 45 sec was followed by thirty cycles of PCR performed using a cycle profile of denaturation at 96° C. for 10 sec, annealing at 55° C. for 30 sec, and extension at 72° C. for 45 sec. 10 μl aliquots of the amplification product were analyzed by electrophoresis in 1.0% agarose gels (NuSieve™, FMC) with ReadyLoad™ 100 bp DNA ladder (GibcoBRL, Denmark) as a size marker.

40 μl aliquots of the PCR product generated as described above were purified using QIAquick™ PCR purification kit (Qiagen, USA) according to the manufacturer's instructions. The purified DNA was eluted in 50 μl of 10 mM Tris-HCl, pH 8.5.

SOE of the CBD from *Cellulomonas fimi* (ATCC 484) cenA Gene and the Termamyl™ Gene Approximately 100–200 ng of the PCR amplified Termamyl™ fragment and the PCR amplified cenA CBD fragment were used in a second round of PCR. SOE of the two fragments was performed in HiFidelity™ PCR buffer (Boehringer Mannheim, Germany) supplemented with 200 μM of each dNTP, 2.6 units of HiFidelity™ Expand enzyme mix.

A touch-down PCR cycling was performed as follows: One incubation at 96° C. for 2 min, 60° C. for 2 min and 72° C. for 45 sec. This cycle was repeated ten times with a 1° C. decrease of the annealing temperature at each cycle.

A third PCR reaction was started by adding 100 pmol of the two flanking primers #8828 and #4576 (vide supra) to amplify the hybrid DNA. PCR was performed by incubating the SOE reaction mixture at 96° C. for 2 min, 55° C. for 30 sec and 72° C. for 45 sec. This was followed by twenty cycles of PCR performed using a cycle profile of denaturation at 96° C. for 10 sec, annealing at 55° C. for 30 sec, and extension at 72° C. for 45 sec. 10 μl aliquots of the amplification product were analyzed by electrophoresis in 1.0% agarose gels (NuSieve™, FMC) with ReadyLoad™ 100 bp DNA ladder (GibcoBRL, Denmark) as a size marker. The SOE fragment had the expected size of 879 bp.

Subcloning of the SOE Fragment Coding for the CBD-Termamyl Hybrid

40 μl of the SOE-PCR product generated as described above was purified using QIAquick™ PCR purification kit (Qiagen, USA) according to the manufacturer's instructions. The purified DNA was eluted in 50 μl of 10 mM Tris-HCl, pH 8.5. 25 μl of the purified PCR fragment was digested with PstI and KpnI, subjected to electrophoresis in 1.0% low gelling temperature agarose (SeaPlaque™ GTG, FMC) gels, and a fragment of 837 bp was excised from the gel and purified using QIAquick™ Gel extraction Kit (Qiagen, USA) according to the manufacturer's instructions. The isolated DNA fragment was then ligated to PstI- and KpnI-digested pDN1981, and the ligation mixture was used to transform competent cells of *B. subtilis* PL2306. Cells were plated on LB agar plates containing Kanamycin (10 μg/ml), 0.4% glucose and 10 mM potassium hydrogen phosphate, and incubated at 37° C. overnight. The next day, colonies were restreaked onto fresh LBPG Kanamycin agar plates and incubated at 37° C. overnight. The following day, single colonies of each clone were transferred to liquid LB medium containing Kanamycin (10 μg/ml) and incubated overnight at 37° C. with shaking at 250 rpm.

Plasmids were extracted from the liquid cultures using QIAgen Plasmid Purification mini kit (Qiagen, USA) according to the manufacturer's instructions. However, the resuspension buffer was supplemented with 1 mg/ml of chicken egg white lysozyme (SIGMA, USA) prior to lysing the cells at 37° C. for 15 minutes. 5 μl samples of the plasmids were digested with PstI and KpnI. The digestions were checked by gel electrophoresis on a 1.5% agarose gel (NuSieve™, FMC). The appearance of a DNA fragment of 837 bp, the same size as seen from the PCR amplification, indicated a positive clone. One positive clone was designated MOL1297.

Expression, Secretion and Functional Analysis of the Fusion Protein

The clone MOL1297 (expressing *C. fimi* cenA CBD fused to the N-terminal of Termamyl™) was incubated for 20 hours in SB medium at 37° C. with shaking at 250 rpm. 1 ml of cell-free supernatant was mixed with 200 µl of 10% Avicel™. The mixture was incubated for 1 hour at 0° C. and then centrifuged for 5 min at 5000×g. The pellet was resuspended in 100 µl of SDS-PAGE buffer, boiled at 95° C. for 5 minutes, centrifuged at 5000×g for 5 minutes, and 25 µl was loaded on a 4–20% Laemmli Tris-Glycine, SDS-PAGE NOVEX gel (Novex, USA). The samples were subjected to electrophoresis in an Xcell™ Mini-Cell (NOVEX, USA) as recommended by the manufacturer. All subsequent handling of gels including staining (Coomassie), destaining and drying, was performed as described by the manufacturer.

The appearance of a protein band of MW approx. 85 kDa indicated expression in *B. subtilis* of the CBD-Termamyl™ fusion.

The encoding sequence for the *C. fimi* cenA CBD-Termamyl hybrid is shown in SEQ ID No. 7 (in which nucleotides 100–441 are the CBD-encoding part of the sequence). The corresponding amino acid sequence of the hybrid is shown in SEQ ID No. 8 (in which amino acid residues 30–147 are the CBD amino acid sequence).

EXAMPLE 4

This example describes the construction of fusion proteins (enzyme hybrid) from a lipase (Lipolase™; *Humicola lanuginosa* lipase) and a CBD. A construction with an N-terminal CBD was chosen, since the N-terminal of the enzyme is far from the active site, whereas the C-terminal is in relatively close proximity to the active site.

pIVI450 Construction (CBD-linker-lipase)

This construct was made in order to express a protein having the *Myceliophthora thermophila* cellulase CBD and linker at the N-terminal of Lipolase™.

A PCR fragment was created using the clone pA2C161 (DSM 9967) containing the *M. thermophila* cellulase gene as template, and the following oligomers as primers:
8202

5' ACGTAGTGGCCACGCTAGGCGAGGTGGTGG 3' (SEQ ID No. 24)

19672

5' CCACACTTCTCTTCCTTCCTC 3' (SEQ ID No. 25)

The PCR fragment was cut with BamHI and BalI, and cloned into pAHL which was also cut with BamHI and BalI just upstream of the presumed signal peptide processing site. The cloning was verified by sequencing (see SEQ ID No. 9).

Removing Linker Between CBD and Lipase

This construct is made so that any linker of interest can be inserted between the CBD and the lipase in order to find an optimal linker.

An NheI site is introduced by the USE technique (Stratagene catalogue No. 200509) between the CBD and linker region in pIVI450, creating pIVI450+NheI site. pIVI450+NheI site is cut with XhoI and NheI, isolating the vector containing the CBD part.

The plasmid pIVI392 is cut with XhoI and NheI, and the fragment containing the Lipolase™ gene (minus signal peptide encoding sequence) is isolated.

The DNA fragments are ligated, generating pIVI450 CBD-NheI site-Lipolase™ containing an NheI site between the CBD and the lipase gene. In this NheI site different linkers can be introduced.

Introduction of Non-glycosylated Linker

The protein expressed from the construct described here contains a construction of the type: CBD-nonglycosylated linker-lipase.

The amino acid sequence of the linker is as follows:

NNNPQQGNPNQGGNNGGGNQGGGNGG (SEQ ID No. 26)

PCR is performed with the following primers:
29315

5' GATCTAGCTAGCAACAATAACCCCCAG-CAGGGCAACCCCAACCAGGGCGGGAA-CAACGGC 3' (SEQ ID No. 27)

29316

5' GATCTAGCTAGCGCCGCCGTTGCCGC-CGCCCTGGTTGCCGCCGCCGTTGTTC-CCGCCCTG 3' (SEQ ID No. 28)

The PCR fragment is cut with NheI, the vector pIVI450 CBD-NheI-Lipolase™ is likewise cut with NheI, and the two fragments are ligated, creating: pIVI450 CBD-Nonglycosylated linker-Lipolase™ (SEQ ID No. 10).

Introduction of *H. insolens* Family 45 Cellulase Linker

The protein expressed from the construct described here contains a construction of the type: CBD-glycosylated linker-lipase.

The amino acid sequence of the linker is as follows:

VQIPSSSTSSPVNQPTSTSTTSTSTTSSPPVQPTTPS (SEQ ID No. 29)

PCR is performed with the following primers:
29313

5' GATACTGCTAGCGTCCAGATCCCCTCCAGC 3' (SEQ ID No. 30)

29314

5' GATACTGCTAGCGCTGGGAGTCGTAGGCTG 3' (SEQ ID No. 31)

The PCR fragment is cut with NheI, the vector pIVI450 CBD-NheI-Lipolase™ is likewise cut with NheI, and the two fragments are ligated, creating: pIVI450 CBD-H. insolens family 45 cellulase linker-Lipolase™ (SEQ ID No. 11).

We claim:

1. A desizing composition comprising: (a) an enzyme hybrid which comprises a catalytically active amino acid sequence of a lipase or an amylase linked to an amino acid sequence comprising a cellulose-binding domain and (b) a wetting agent.

2. A process for desizing a cellulose-containing textile, comprising treating the textile with an enzyme hybrid which comprises a catalytically active amino acid sequence of a lipase or an amylase linked to an amino acid sequence comprising a cellulose-binding domain.

3. The process according to claim 2, wherein the amino acid sequence of said amylase is of an α-amylase obtainable from a species of Bacillus.

4. The process according to claim 3, wherein the α-amylase is obtainable from *Bacillus licheniformis*.

5. The process according to claim 2, wherein said enzyme hybrid comprises the catalytically active amino acid sequence of an amylase and said enzyme hybrid is employed in an amount corresponding to an amylase activity in the range of between 1 and 5000 KNU per liter of desizing liquor.

6. The process according to claim 2, wherein the amino acid sequence of said lipase is of a lipase obtainable from a species of Humicola, Candida, Pseudomonas or Bacillus.

7. The process according to claim 2, wherein said enzyme hybrid comprises the catalytically active amino acid sequence of a lipase and said enzyme hybrid is employed in an amount corresponding to a lipase activity in the range of between 10 and 20000 LU per liter of desizing liquor.

8. The process according to claim 2, wherein the cellulose-binding domain is obtainable from a cellulase, a xylanase, a mannanase, an arabinofuranosidase, an acetylesterase or a chitinase.

9. The process according to claim 2, wherein the enzyme hybrid is obtained by a method comprising growing a transformed host cell containing an expression cassette which comprises a DNA sequence encoding the enzyme hybrid, whereby the enzyme hybrid is expressed.

* * * * *